(12) United States Patent
Kato

(10) Patent No.: US 9,810,654 B2
(45) Date of Patent: Nov. 7, 2017

(54) FUEL PROPERTY MEASURING DEVICE

(71) Applicant: AISAN KOGYO KABUSHIKI KAISHA, Aichi-ken (JP)

(72) Inventor: Nobuhiro Kato, Aichi-ken (JP)

(73) Assignee: AISAN KOGYO KABUSHIKI KAISHA, Obu-Shi, Aichi-ken (JP)

( * ) Notice: Subject to any disclaimer, the term of this patent is extended or adjusted under 35 U.S.C. 154(b) by 786 days.

(21) Appl. No.: 13/845,371

(22) Filed: Mar. 18, 2013

(65) Prior Publication Data
US 2013/0257457 A1 Oct. 3, 2013

(30) Foreign Application Priority Data

Mar. 29, 2012 (JP) .................................. 2012-077912
Feb. 5, 2013 (JP) .................................. 2013-020288

(51) Int. Cl.
*G01N 11/00* (2006.01)
*G01N 27/22* (2006.01)
*G01N 33/28* (2006.01)

(52) U.S. Cl.
CPC ......... *G01N 27/22* (2013.01); *G01N 33/2852* (2013.01)

(58) Field of Classification Search
CPC ......... F02D 2200/0611; F02D 2200/06; F02D 2200/0606; F02D 2200/0602; F02D 2200/0614; F02D 19/0628; F02D 19/0634; F02D 19/0665; F02D 19/087; F02D 29/04; F02D 33/003; F02D 19/0626; F02M 37/025; F02M 37/103; F02M 37/106;

(Continued)

(56) References Cited

U.S. PATENT DOCUMENTS 4,905,655 A * 3/1990 Maekawa ............ F02D 19/0684
123/1 A
2006/0243248 A1* 11/2006 Kawanishi .......... F02D 41/0025
123/406.12

(Continued)

FOREIGN PATENT DOCUMENTS

CN 101503985 A 8/2009
CN 101750464 A 6/2010

(Continued)

OTHER PUBLICATIONS

Office Action dated Jan. 7, 2015 in Chinese Patent Application No. 201310109870.8, with English language translation, 11 pages.

(Continued)

*Primary Examiner* — John Fitzgerald
*Assistant Examiner* — Rodney T Frank
(74) *Attorney, Agent, or Firm* — Vierra Magen Marcus LLP

(57) ABSTRACT

A measuring device for measuring a property of fuel supplied from a fuel tank to a combustion apparatus, may comprise a fuel pump that sucks the fuel in a fuel tank and pumps the fuel toward a combustion apparatus, a fuel discharging portion that discharges the fuel from the fuel pump into the fuel tank, a fuel-measuring storage chamber that receives the fuel discharged from the fuel discharging portion and a pair of electrodes disposed within the fuel-measuring storage chamber so as to measure capacitance.

20 Claims, 20 Drawing Sheets

(58) Field of Classification Search
CPC . F02M 37/0082; G01F 23/263; G01F 23/268; G01N 27/226; Y10T 137/86187
USPC ........................................................ 73/53.01
See application file for complete search history.

(56) References Cited

U.S. PATENT DOCUMENTS

| | | | |
|---|---|---|---|
| 2009/0193873 A1* | 8/2009 | Nakamura | F02D 33/003 73/31.05 |
| 2010/0116361 A1* | 5/2010 | Furuhashi | B60K 15/077 137/398 |
| 2010/0229638 A1 | 9/2010 | Nakamura et al. | |
| 2010/0244857 A1 | 9/2010 | Nakamura | |
| 2010/0332108 A1 | 12/2010 | Kato et al. | |
| 2012/0126835 A1 | 5/2012 | Nakamura | |
| 2012/0222473 A1 | 9/2012 | Kita et al. | |
| 2013/0276532 A1 | 10/2013 | Kato | |
| 2013/0340496 A1 | 12/2013 | Wakao et al. | |

FOREIGN PATENT DOCUMENTS

| | | |
|---|---|---|
| CN | 103270281 A | 8/2013 |
| CN | 103364050 A | 10/2013 |
| JP | H01239444 | 9/1989 |
| JP | H03249552 A | 11/1991 |
| JP | H09-195872 A | 7/1997 |
| JP | 2004293524 A | 10/2004 |
| JP | 2009198450 A | 9/2009 |
| JP | 2010210563 A | 9/2010 |
| JP | 2010-223830 | 10/2010 |
| JP | 2011-164085 | 8/2011 |
| JP | 2011153561 A | 8/2011 |
| JP | 2012-108030 | 6/2012 |
| WO | 2011052139 A1 | 5/2011 |

OTHER PUBLICATIONS

English abstract of CN101750464, dated Jun. 23, 2010.
Family List of Japanese Patent Application No. JP 2010-223830.
English Translation of Abstract of Japanese Patent Application No. JP 2010-223830.
Machine Translation of Japanese Patent Application No. JP 2010-223830 prepared by the Japanese Patent Office.
English Translation of Abstract of Japanese Patent Application No. JP 2011-164085.
Machine Translation of Japanese Patent Application No. JP 2011-164085 prepared by the Japanese Patent Office.
Family List of Japanese Patent Application No. JP 2012-108030.
English Translation of Abstract of Japanese Patent Application No. JP 2012-108030.
Machine Translation of Japanese Patent Application No. JP 2012-108030 prepared by the Japanese Patent Office.
Office Action dated Sep. 14, 2015 in Chinese Patent Application No. 201310109870.8.
Office Action dated Mar. 1, 2016 in Japanese Patent Application No. 2013-020288.

* cited by examiner

FUEL PROPERTY MEASURING DEVICE

CROSS-REFERENCE TO RELATED APPLICATIONS

This application claims priority to Japanese Patent Application No. 2012-077912 filed on Mar. 29, 2012, and Japanese Patent Application No. 2013-020288 filed on Feb. 5, 2013, the contents of which are hereby incorporated by reference into the present application.

TECHNICAL FIELD

The present specification discloses a device for measuring capacitance capacitance between a pair of electrodes) of an electrode pair that is immersed in fuel.

DESCRIPTION OF RELATED ART

Alcohol blended fuel has recently come into wide use. In the case of alcohol blended fuel, an alcohol content is rust constant. Combustion apparatuses such as an engine need to be supplied with an amount of fuel corresponding to an optimum air-fuel ratio, and the optimum amount changes according to the alcohol content. Thus, it is necessary to measure the alcohol content of fuel supplied from a fuel tank to the combustion apparatus.

A relative permittivity of alcohol blended fuel changes according to an alcohol content and temperature. The alcohol content may be measured by immersing a pair of electrodes into the alcohol blended fuel and measuring the capacitance between the electrodes and temperature. Japanese Patent Application Publication No. 2011-164085 discloses a technique of measuring capacitance between a pair of electrodes immersed into alcohol blended fuel and temperature to thereby measure an alcohol content.

Those that may be detected from the capacitance between the pair of electrodes immersed into fuel are not limited to the alcohol content. The capacitance between the pair of electrodes immersed into fuel is measured in some cases in order to measure fuel properties such as gasoline quality or the content of engine oil mixed into fuel.

SUMMARY

In the case of the alcohol blended fuel, since the alcohol content is not constant, the alcohol content may often change according to the location within a fuel tank immediately after fueling. The other fuel properties may also change depending on the location within the fuel tank immediately after fueling. It is difficult to appropriately measure the property of fuel supplied from a fuel tank to a combustion apparatus just by providing a pair of electrodes in the fuel tank.

In the technique disclosed in Japanese Patent Application Publication No. 2011-164085, a pair of electrodes is immersed into the fuel that is pumped from a fuel pump to a combustion apparatus. According to the technique disclosed in Japanese Patent Application Publication No. 2011-164085, even when the fuel property changes according to the location within the fuel tank, it is possible to measure the property of the fuel supplied from the fuel tank to the combustion apparatus.

However, high pressure acts on the fuel that is pumped from the fuel pump. According to the technique of disposing the pair of electrodes between the fuel pump and the combustion apparatus, since the high pressure is applied to the pair of electrodes, or a substrate or the like in which the pair of electrodes is formed, the electrode or the substrate or the like need to have a pressure-resistant structure. According to the technique of disposing the pair of electrodes between the fuel pump and the combustion apparatus, the requirements for the electrodes, or the substrate or the like become strict.

The present application discloses a technique for measuring properties of fuel supplied from a fuel tank to a combustion apparatus even when the fuel properties change depending on the location within the fuel tank, acid reducing load applied to electrodes, or a substrate or the like.

The present application discloses a measuring device for measuring a property of fuel supplied from a fuel tank to a combustion apparatus. The measuring device may comprise a fuel tank that stores fuel, a fuel pump that sucks the fuel in the fuel tank and pumps the fuel toward the combustion apparatus, a fuel discharging portion that discharges the fuel from the fuel pump into the fuel tank, a fuel-measuring storage chamber that receives the fuel discharged from the fuel discharging portion and a pair of electrodes disposed within the fuel-measuring storage chamber so as to measure capacitance.

In the above measuring device, since the capacitance is measured within the fuel-measuring storage chamber that receives fuel delivered from the fuel pump, the property of the fuel supplied from the fuel tank to the combustion apparatus may be measured even when the fuel properties change according to the location within the fuel tank. Moreover, since the capacitance is measured within the fuel-measuring storage chamber that receives the fuel discharged from the fuel discharging portion, the pressure of the fuel applied to the electrodes may be decreased as compared to a case where electrodes are disposed on a passage along which the fuel is supplied from the fuel tank to the combustion apparatus. According to this configuration, the property of the fuel supplied from the fuel tank to the combustion apparatus may be measured even when the fuel properties change according to the location within the fuel tank while suppressing the load applied to the electrodes.

Further, the present application discloses another measuring device for measuring a property of fuel supplied from a fuel tank to a combustion apparatus. The measuring device may comprise a fuel pump that sucks the fuel in a fuel tank and pumps the fuel toward a combustion apparatus, a fuel discharging portion that discharges the fuel from the fuel pump into the fuel tank, a fuel-measuring storage chamber that receives the fuel discharged from the fuel discharging portion, and a pair of electrodes disposed within the fuel-measuring storage chamber so as to measure capacitance.

According to this configuration, the pressure of the fuel applied to the electrodes may be decreased as compared to a case where electrodes are disposed on a passage along which the fuel is supplied from the fuel tank to the combustion apparatus. According to this configuration, the property of the fuel supplied from the fuel tank to the combustion apparatus may be measured even when the fuel properties change according to the location within the fuel tank while suppressing the load applied to the electrodes.

DETAILED DESCRIPTION

Figure 1:
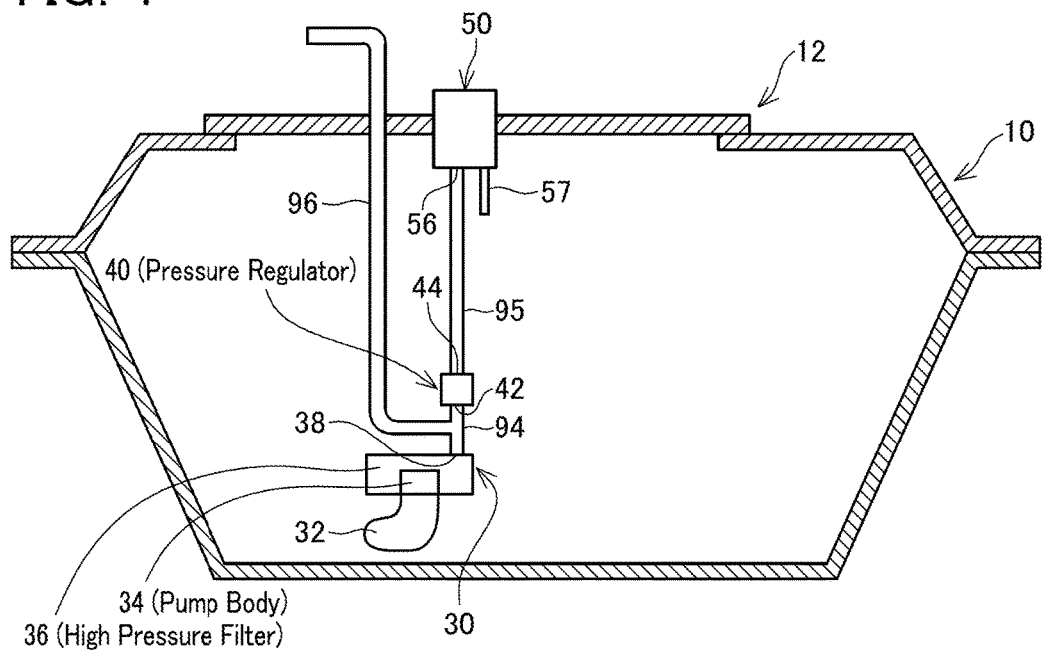
FIG. 1 shows a configuration around a fuel tank according to a first embodiment.

First, some of the features of embodiments described below will be described. The features described herein each independently have technical usefulness.

(Feature 1) The fuel discharging portion may comprise a pressure regulator disposed between the fuel pump and the combustion apparatus so as to regulate pressure of the fuel pumped toward the combustion apparatus to a predetermined value by discharging surplus fuel. According to this configuration, since the capacitance is measured within the fuel-measuring storage chamber that receives the fuel discharged from the pressure regulator, the pressure of the fuel flowing into the fuel-measuring storage chamber may be decreased. According to this configuration, the properties of the fuel supplied from the fuel tank to the combustion apparatus may be measured even when the fuel properties change according to the location within the fuel tank while suppressing the load applied to the electrodes.

(Feature 2) The fuel discharging portion may comprise a branch passage that branches off from a fuel supply pipe for supplying fuel from the fuel pump to the combustion apparatus and a decompressing portion that decreases the pressure of the fuel in the branch passage. According to this configuration, since the capacitance is measured within the fuel-measuring storage chamber that receives the fuel decompressed by the decompressing portion, the properties of the fuel supplied from the fuel tank to the combustion apparatus may be measured even when the fuel properties change according to the location within the fuel tank while suppressing the load applied to the electrodes.

(Feature 3) The fuel discharging portion may comprise a discharge passage that extends from a vapor jet disposed in the fuel pump to the inside of the fuel tank. The vapor jet may be used for discharging vapor in the fuel pump, from the fuel pump into the fuel tank. According to this configuration, since the capacitance is measured within the fuel-measuring storage chamber that receives the fuel discharged from the vapor jet, the pressure of the fuel flowing into the fuel-measuring storage chamber may be decreased. According to this configuration, the properties of the fuel supplied from the fuel tank to the combustion apparatus may be measured even when the fuel properties change according to the location within the fuel tank while suppressing the load applied to the electrodes.

(Feature 4) The fuel-measuring storage chamber has a shape for implementing a fuel storage function with which the fuel does not leak from the fuel-measuring storage chamber when the fuel pump stops. According to this configuration, a state where the electrodes are immersed into fuel may be maintained when the fuel pump is stopped. Due to this, a foreign contamination such as dust may be prevented from adhering to the electrodes. Moreover, the electrodes are stably immersed into the fuel that is open to the atmosphere, and the load applied to the electrodes is reduced.

(Feature 5) The fuel-measuring storage chamber may comprise a bottomed cylinder that accommodates the pair of electrodes. According to this configuration, if the pair of electrodes is accommodated in the cylinder, fuel may not leak from the surrounding of the electrodes when the fuel pump stops. Due to this, a foreign contamination such as dust may be prevented from adhering to the electrodes. Moreover, the electrodes are stably immersed into the fuel that is open to the atmosphere, and the load applied to the electrodes is reduced. The shape having a fuel storage function is not limited to the bottomed cylinder. For example, a cylinder of which only the upper end is closed and the lower end is open may be used. Even when the lower end is open, since there is no entrance port through which air is replaced with fuel, the fuel may not leak from the inside of the cylinder.

(Feature 6) The pair of electrodes may be surrounded by an electromagnetic shield. According to this configuration, ambient electromagnetic noise is electromagnetically shielded and is prevented from affecting the measurement result of the capacitance. The electromagnetic shield that surrounds the pair of electrodes may be a metallic cylinder, a resin cylinder of which the inner or outer surface is plated with metal, or a resin cylinder of which the inner or outer surface is coated with metal-containing paint or metal-containing ink.

(Feature 7) The fuel-measuring storage chamber and the pair of electrodes may be fixed to a set plate that closes an opening formed in the fuel tank. According to this configuration, the capacitance measuring device may be easily provided within the fuel tank. An electronic circuit of the capacitance measuring device, the fuel pump, a reservoir tank, the pressure regulator, the liquid level measuring device, a case for accommodating the liquid level measuring device, and the like may be fixed to the set plate.

(Feature 8) The measuring device may further comprise a reserve cup that accommodate the fuel pump in the fuel tank, a jet pump that delivers fuel outside the reserve cup into the reserve cup by utilizing a speed of the fuel discharged from the fuel discharging portion and a flow passage that extends from the fuel discharging portion and reaches the jet pump via the fuel-measuring storage chamber. According to this configuration, it is not necessary to provide a new configuration for delivering fuel to the jet pump.

(Feature 9) The measuring device may further comprise a reserve cup that accommodate the fuel pump in the fuel tank, a jet pump that delivers fuel outside the reserve cup into the reserve cup by utilizing a speed of the fuel discharged from the fuel discharging portion and a first flow passage that extends from the fuel discharging portion to the fuel-measuring storage chamber, and a second flow passage that extends from the fuel discharging portion to the jet pump. According to this configuration, it is not necessary to provide a new configuration for delivering fuel to the jet pump. Moreover, the flow passage for delivering fuel to the jet pump and the flow passage for delivering fuel to the fuel-measuring storage chamber may be provided separately. Due to this, the pressure of the fuel delivered to the jet pump and the pressure of the fuel delivered to the fuel-measuring storage chamber may be individually regulated.

(Feature 10) The measuring device may further comprise a three-way valve disposed at a branching point between the first flow passage and the second flow passage. The three-way valve switches between a state where the fuel is delivered from the pressure regulator to the fuel-measuring storage chamber and a state where the fuel is delivered from the pressure regulator to the jet pump. Thus, the fuel to the fuel-measuring storage chamber as necessary while maintaining the sucking action of the jet pump may be delivered.

(Feature 11) A flow passage area of at least a portion of the first flow passage may be smaller than a flow passage area of the second flow passage. According to this configuration, the pressure of the fuel flowing into the fuel-measuring storage chamber may be reduced.

(Feature 12) The measuring device may further comprise a flow passage regulating portion that is disposed in the first flow passage and comprises a valve, an aperture, or a combination thereof. According to this configuration, the fuel flowing into the fuel-measuring storage chamber may be regulated using the flow passage regulating portion.

(Feature 13) The flow passage regulating portion may be configured to be integrated with a set plate that closes an opening formed in the fuel tank. According to this configuration, the flow passage regulating portion in the fuel tank may be easily provided.

(Feature 14) The measuring device may further comprise a communication hole disposed at an intermediate position of the second flow passage so as to allow the second flow passage to communicate with the fuel tank. In a case where the fuel pump stops after driving, the flow passage that extends from the fuel discharging portion to the jet pump is filled with fuel. As a result, due to a siphon phenomenon, the fuel in the flow passage extending from the fuel discharging portion to jet pump may flow from the jet pump toward the fuel pump. Due to the communication passage, the occurrence of the siphon phenomenon may be suppressed.

(Feature 15) The branch passage and the decompressing portion may be configured to be integrated with a set plate that closes an opening formed in the fuel tank. According to this configuration, the branch passage and the decompressing portion in the fuel tank may be easily provided.

(Feature 16) The measuring device may further comprise a valve mechanism that is disposed in the branch passage so as to close a fuel discharge passage in a case where pressure applied from the fuel to the valve mechanism is smaller than a predetermined value, and to open the fuel discharge passage in a case where the pressure applied from the fuel to the valve mechanism is the predetermined value or more. According to this configuration, in a case where the pressure of the fuel in the fuel supply pipe is smaller than a predetermined value, the fuel is prevented from being supplied to the branch passage. As a result, a decrease in the pressure of the fuel supplied to the combustion apparatus through the fuel supply pipe may be suppressed.

(Feature 17) The measuring device may further comprise a liquid level measuring device, a case that accommodates the liquid level measuring device and has fuel permeating properties so that liquid levels inside and outside the case are equalized and a flow passage that extends from the fuel discharging portion and reaches the case via the fuel-measuring storage chamber. According to this configuration, the fuel of which the capacitance is measured is delivered to the liquid level measuring device. According to this configuration, the liquid level measuring device may convert the value measured by the liquid level measuring device into a liquid level based on the permittivity of the fuel accurately measured by the capacitance measuring device.

(Feature 18) The measuring device may further comprise a reserve cup disposed in the fuel tank so as to accommodate the fuel pump, a jet pump that delivers fuel outside the reserve cup into the reserve cup by utilizing a speed of the fuel discharged from the fuel discharging portion and a flow passage that extends from the fuel discharging portion and reaches the jet pump via the fuel-measuring storage chamber. A suction port of the jet pump communicates with the inside of the case. According to this configuration, the fuel present in the chamber that stores capacitance measurement fuel and the fuel present in the case that accommodates the liquid level measuring device are quickly homogenized.

(Feature 19) The combustion apparatus may be an engine. However, the combustion apparatus is not particularly limited and typically corresponds to an engine. An electronic circuit for outputting a value corresponding to the capacitance may be incorporated into the measuring device and may be provided separately from the measuring device. The measurement result output from the electronic circuit may be the capacitance itself, may be a value obtained by converting the capacitance into the permittivity of fuel, and may be a value obtained by converting the capacitance into the fuel property such as an alcohol content by taking the effect of temperature or the like into consideration. Moreover, the output value may be an indication of a voltage value or a current value.

(Feature 20) A voltage or a current proportional to the capacitance between the pair of electrodes may be output.

(Feature 21) A voltage or a current proportional to the permittivity of fuel that is converted from the capacitance may be output.

(Feature 22) A voltage or a current proportional to an alcohol content that is converted from the capacitance and the temperature may be output.

(Feature 23) The fuel-measuring storage chamber may be sealed so that the fuel open to the atmosphere does not leak.

(First Embodiment)

FIG. 1 shows a configuration around a fuel tank according to the first embodiment. A fuel pump 30 is accommodated in a fuel tank 10. The fuel pump 30 is configured such that fuel filtered by a low pressure filter 32 is sucked into a pump body 34, the sucked fuel is filtered by a high pressure filter 36, and the filtered pressurized fuel is delivered from an outlet port 38. A pipe 94 is connected to the outlet port 38, and an inlet port 42 of a pressure regulator 40 is connected to the pipe 94. The pressure regulator 40 comprises a valve which allows the inlet port 42 and the outlet port 44 to communicate with each other when the pressure of the inlet port 42 becomes a predetermined value or more. When the pressure of the inlet port 42 becomes the predetermined value or smaller, the valve is closed so that the inlet port 42 and the outlet port 44 do not communicate with each other. The pressure regulator 40 regulates the pressure of the inlet port 42 and the fuel in the pipe 94 to be constant by discharging surplus fuel from the outlet port 44. A pipe 96 branches of from the pipe 94, and the pipe 96 is connected to an engine via a delivery pipe and an injector. The fuel in the fuel tank 10 is pumped to the engine with the pressure regulated to be constant by the fuel pump 30 and the pressure regulator 40.

A pipe 95 is connected to the outlet port 44 of the pressure regulator 40, and a capacitance measuring device 50 is connected to the pipe 95. The fuel discharged from the outlet port 44 of the pressure regulator 40 is delivered to the capacitance measuring device 50, in which the capacitance is measured, and is then returned from the outlet port 57 to the fuel tank 10.

The fuel pump 30, the pressure regulator 40, the capacitance measuring device 50, the pipes 94, 95, and 96, and the like are fixed to a set plate 12. The set plate 12 is fixed to the fuel tank 10 to close the opening of the fuel tank 10 and aligns the fuel pump 30, the pressure regulator 40, the capacitance measuring device 50, the pipes 94, 95, and 96, and the like within the fuel tank 10.

Figure 9A:
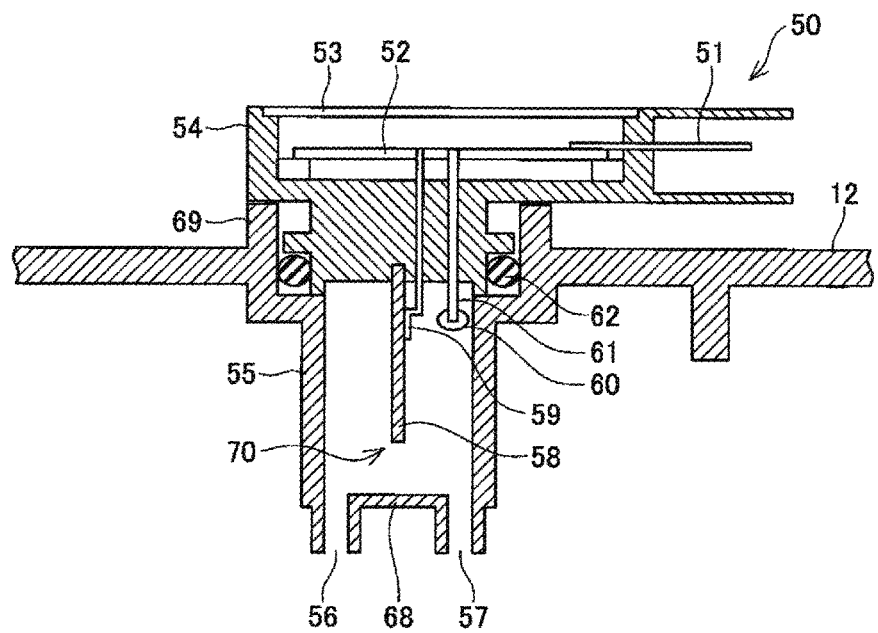
FIGS. 9A and 9B show a configuration of a capacitance measuring device according to the first embodiment.

FIG. 9A shows the structure of the capacitance measuring device 50. A cylindrical wall 55 that extends downward from the set plate 12 is formed in a portion of the set plate 12, and the inlet port 56 and the outlet port 57 are formed in a bottom plate 68 of the wall 55. A cylindrical wall 69 that extends upward from the set plate 12 is also formed in a portion of the set plate 12. A sensor body 54 is inserted into the inner side of the cylindrical wall 69. An O-ring 62 is hermetically maintained between the cylindrical wall 69 and the sensor body 54.

Figure 9B:
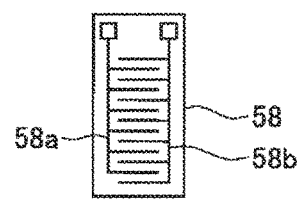

A sensor substrate 58 is formed on the sensor body 54 so as to face downward. As shown in FIG. 9B, a pair of electrodes having such a shape that comb-shaped electrodes 58a and 58b face each other is formed on the Tight surface of the sensor substrate 58. A pair of conductive pieces 59a and 59b (collectively denoted by number 59 in FIG. 9A) electrically connected to the pair of electrodes 58a and 58b extends upward while passing through the sensor body 54 and is connected to a circuit substrate 52.

Moreover, a temperature measuring thermistor 60 is disposed under the sensor body 54. A pair of conductive pieces 61a and 61b (collectively denoted by number 61 in FIG. 9A) electrically connected to the resistor 60 extends upward while passing through the sensor body 54 and is connected to the circuit substrate 52.

Fuel present around the sensor substrate 58, that is, the fuel filled inside the cylinder 55 tills a space of which the upper side is hermetically sealed, and fuel will not leak from the surrounding of the sensor substrate 58. The space surrounded by the cylinder 55, the sensor body 54, and the bottom 68 forms a fuel-measuring storage chamber 70, and the fuel-measuring storage chamber 70 has such a shape that fuel will not leak from the fuel-measuring storage chamber 70 even when the fuel pump 30 stops.

A circuit for charging and discharging current to and from a pair of electrodes 58a and 58b, a circuit for obtaining a value proportional to the capacitance between the pair of electrodes 58a and 58b from a discharge current or a charging current during the discharging or charging, a circuit for obtaining a value proportional to the resistance of the thermistor 60, and a circuit for outputting a value proportional to an alcohol content in the fuel from the value proportional to the capacitance and the value proportional to the resistance are mounted on the circuit substrate 52, and the value proportional to the alcohol content is output to a terminal pin 51. The circuit substrate 52 is accommodated in a space closed by a lid 53.

When an engine is started immediately after fueling, there is a case where the property of the fuel supplied from the fuel pump 30 and the fuel tank 10 to the engine is not identical to the property of the fuel present at a distance from the fuel pump 30. Unless the position of the sensor substrate 58 placed in the fuel pump 30 is not taken into special account, the property of the fuel supplied from the fuel pump 30 and the fuel tank 10 to the engine may not be identical to the property of the fuel measured by the sensor substrate 58.

In the case of the embodiment shown in FIG. 1 and FIGS. 9A and 9B, the sensor substrate 58 is immersed into the fuel discharged from the pressure regulator 40 in order to regulate the pressure of the fuel delivered from the fuel pump 30 and supplied to the engine so as to have a predetermined value. Thus, even when the fuel properties change according to the location within the fuel tank 10, it is possible to measure the properties of the fuel supplied from the fuel tank 10 to the engine. Moreover, since the fuel discharged from the pressure regulator 40 is received into the fuel-measuring storage chamber 70, high-pressure fuel will not act on the sensor substrate 58 or the like. Thus, it is possible to reduce the load applied to the sensor substrate 58 or the like and to obtain satisfactory durability for a long period. Since only low-pressure fuel that is open to the atmosphere is introduced into the fuel-measuring storage chamber 70, leakage can be easily prevented by the 0-ring 64.

Hereinafter, another embodiment of the structure around the fuel tank 10 will be described. After that, another embodiment of the capacitance measuring device 50 will be described. Constituent components that are the same as or similar to the above-described constituent components will be denoted by the same reference numerals, and redundant description thereof will not be provided.

(Second Embodiment of Structure Around Fuel Tank 10)

Figure 2:
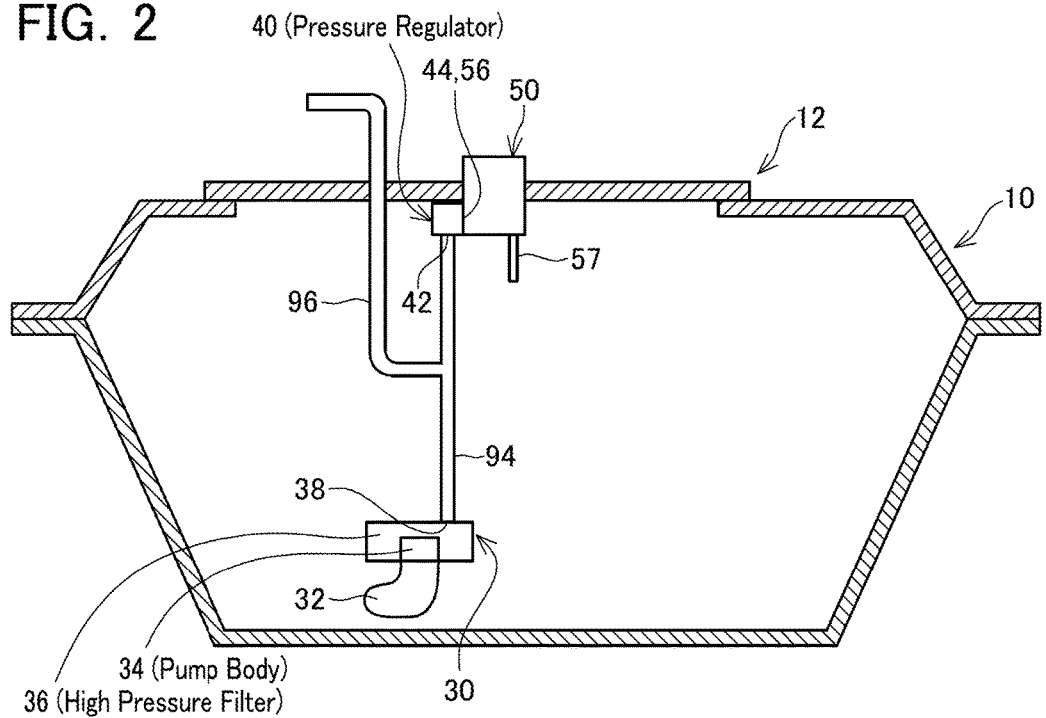
FIG. 2 shows a configuration around a fuel tank according to a second embodiment.

As shown in FIG. 2, in the second embodiment, the pressure regulator 40 is directly fixed to the set plate 12. Moreover, the outlet port 44 of the pressure regulator 40 is directly connected to the inlet port 56 of the capacitance measuring device 50, and the fuel pipe 95 is not used.

According to this embodiment, the fuel discharged from the pressure regulator 40 reaches the capacitance measuring device 50 in a short time. The fuel measured by the capacitance measuring device 50 and the fuel supplied to the engine are easily homogenized.

(Third Embodiment of Structure Around Fuel Tank 10)

Figure 3:
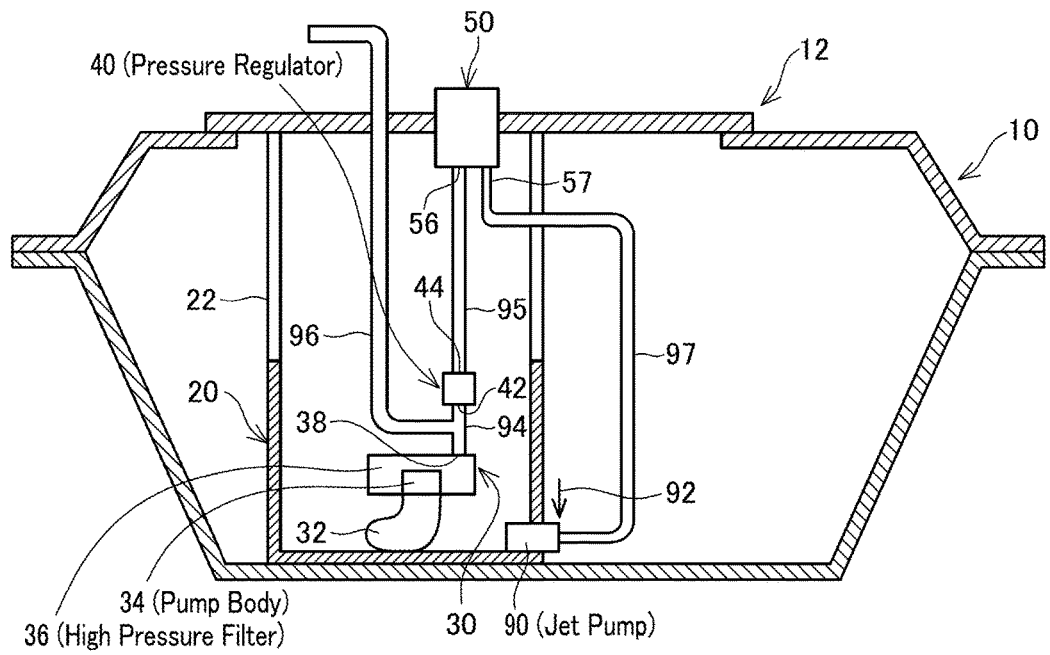
FIG. 3 shows a configuration around a fuel tank according to a third embodiment.

As shown in FIG. 3, in the third embodiment, the fuel tank 10 comprises a reserve cup 20 that accommodates the fuel pump 30 and a jet pump 90 that sends fuel outside the reserve cup 20 into the reserve cup 20. Since the reserve cup 20 and the jet pump 90 are included, it is possible to maintain a high liquid level around the fuel pump 30 even when the amount of fuel remaining in the fuel tank 10 is small.

The reserve cup 20 is fixed to the set plate 12 by a support 22. The jet pump 90 sends the fuel outside the reserve cup 20 into the reserve cup 20 by utilizing the speed of the fuel that is pumped from the fuel pump 30 and discharged from the pressure regulator 40. For example, the jet pump 90 has a diffuser structure so that when fuel discharged from the pressure regulator 40 passes through the diffuser structure, the fuel outside the reserve cup 20 is sucked into the jet pump 90 as indicated by arrow 92, and the fuel sucked from the outside of the reserve cup 20 is sent into the reserve cup 20 together with the fuel discharged from the pressure regulator 40.

In this embodiment, the fuel discharged from the pressure regulator 40 is delivered to the capacitance measuring device 50, and the fuel having passed through the capacitance measuring device 50 is delivered from the fuel pipe 97 to the jet pump 90.

(Fourth Embodiment of Structure Around Fuel Tank 10)

Figure 4:
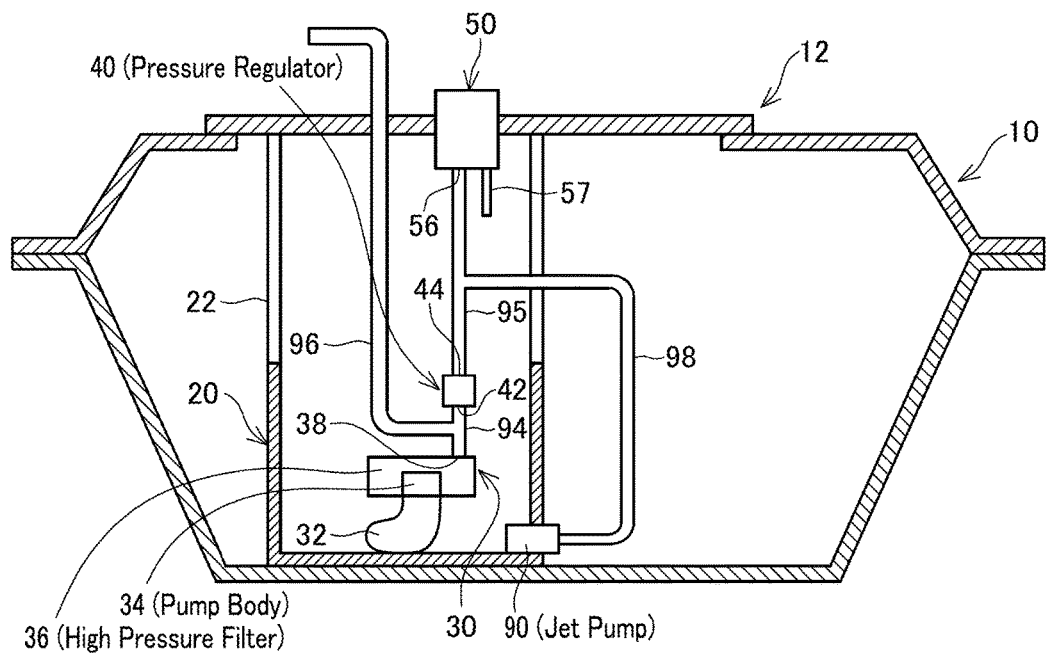
FIG. 4 shows a configuration around a fuel tank according to a fourth embodiment.

As shown in FIG. 4, in the fourth embodiment, a fuel pipe 98 that delivers fuel to the jet pump 90 branches off from the fuel pipe 95 that delivers the fuel discharged from the pressure regulator 40 to the capacitance measuring device 50. A portion of the fuel discharged from the pressure regulator 40 is delivered to the capacitance measuring device 50, and the other portion thereof is delivered to the jet pump 90.

(Fifth Embodiment of Structure Around Fuel Tank 10)

Figure 5:
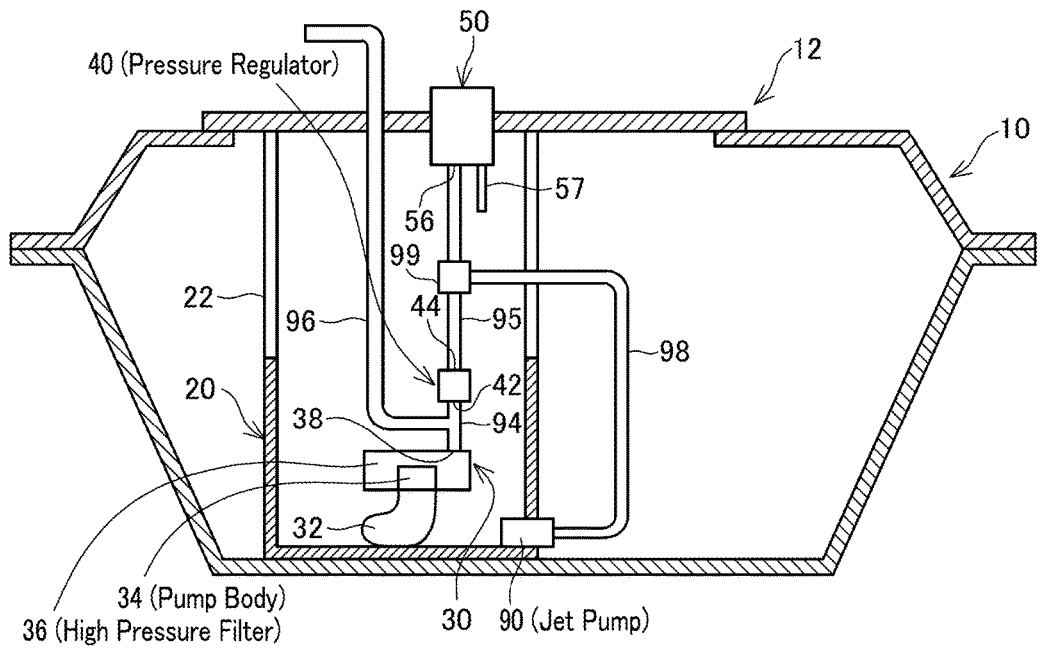
FIG. 5 shows a configuration around a fuel tank according to a fifth embodiment.

As shown in FIG. 5, in the fifth embodiment, a tree-way valve 99 is provided at the branching point between the fuel pipe 95 that delivers the fuel discharged from the pressure regulator 40 to the capacitance measuring device 50 and the fuel pipe 98 that delivers the fuel discharged from the pressure regulator 40 to the jet pump 90. The three-way valve 99 switches between a state where an entire amount of the fuel discharged from the pressure regulator 40 is delivered to the capacitance measuring device 50 and a state where an entire amount of the fuel discharged from the pressure regulator 40 is delivered to the jet pump 90. When the capacitance (that is, permittivity of fuel) is not measured, it is possible to deliver the entire amount of the fuel discharged from the pressure regulator 40 to the jet pump 90 and to efficiently deliver the fuel outside the reserve cup 20 into the reserve cup 20.

(Sixth Embodiment of Structure Around Fuel Tank 10)

Figure 6:
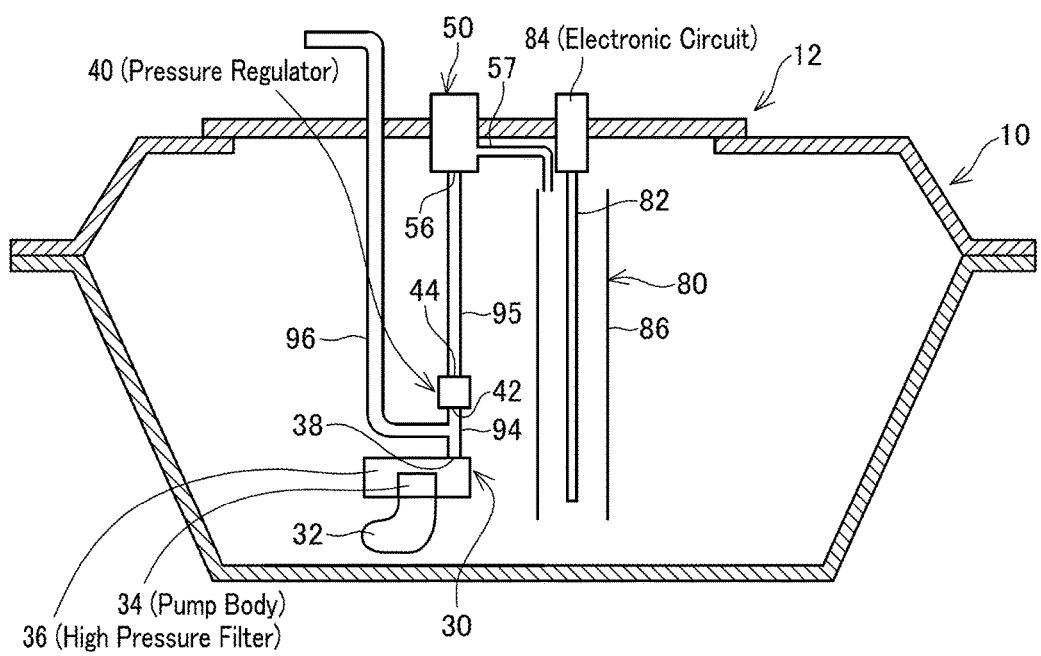
FIG. 6 shows a configuration around a fuel tank according to a sixth embodiment.

As shown in FIG. 6, in the sixth embodiment, the fuel tank 10 comprises a liquid level measuring device 80 that measures the liquid level inside the fuel tank 10 from the capacitance between a pair of electrodes. The liquid level measuring device 80 comprises a liquid level measuring sensor substrate 82, and a pair of comb-shaped electrodes substantially the same as that described in FIG. 9B is formed on the liquid level measuring sensor substrate 82. In the capacitance measuring device 50, the pair of comb-shaped electrodes 58a and 58b is entirely immersed into fuel, and the capacitance thereof is determined by the permittivity of the fuel. In contrast, in the liquid level measuring device 80, a pair of comb-shaped electrodes is partially immersed into fuel, and the remaining portion is exposed from the fuel. The capacitance measured by the liquid level measuring device 80 is determined by the ratio of the immersed portion to the exposed portion determined by a liquid level and the permittivity of the fuel. In order to obtain a liquid level from the capacitance measured by the liquid level measuring device 80, the permittivity of the fuel needs to be known.

As described above, in the case of alcohol blended fuel, since the alcohol content is not constant, the fuel inside a fuel tank immediately after fueling is often not homogenized. Thus, there is a case where the quality of fuel measured by the capacitance measuring device 50 is different from the quality of fuel measured by the liquid level measuring device 80. In this case, when the capacitance measured by the liquid level measuring device 80 is converted into a liquid level using the permittivity of the fuel measured by the capacitance measuring device 50, an incorrect liquid level is obtained.

To solve this problem, in the sixth embodiment, the liquid level measuring device 80 is immersed into the fuel measured by the capacitance measuring device 50. To realize this, in the sixth embodiment, a case 86 that surrounds the liquid level measuring device 80 is provided so that the fuel having passed through the capacitance measuring device 50 is returned into the case 86. The case 86 has open upper and lower ends, for example, and the liquid levels inside and outside the case 86 are maintained to be equal.

According to the above description, it is possible to obtain such a relation that the quality of the fuel measured by the capacitance measuring device 50 is identical to the quality of the fuel measured by the liquid level measuring device 80. As a result, it is possible to obtain a correct liquid level by converting the capacitance measured by the liquid level measuring device 80 into a liquid level using the permittivity of the fuel measured by the capacitance measuring device 50.

Reference numeral 84 shown in FIG. 6 is an electronic circuit 84 connected to the liquid level measuring sensor substrate 82 and also connected to the capacitance measuring device 50. The electronic circuit 84 performs a process of measuring the capacitance obtained by the liquid level measuring sensor substrate 82 and converting the capacitance into a liquid level using the permittivity of the fuel measured by the capacitance measuring device 50 and outputs a value proportional to the obtained liquid level. The electronic circuit 84, the liquid level measuring sensor substrate 82, and the case 86 are fixed to the set plate 12.

The case 86 may equalize the liquid levels inside and outside the case 86 by opening the upper and lower ends thereof. The case 86 may equalize the liquid levels inside and outside the case 86 by forming a vertically extending slit in the wall of the case 86. The case 86 may equalize the liquid levels inside and outside the case 86 by forming a group of vertically arranged openings in the wall of the case 86. Alternatively, the case 86 may equalize the liquid levels inside and outside the case 86 by forming the same using a fuel permeating material such as non-woven fabric.

(Seventh Embodiment of Structure Around Fuel Tank 10)

Figure 7:
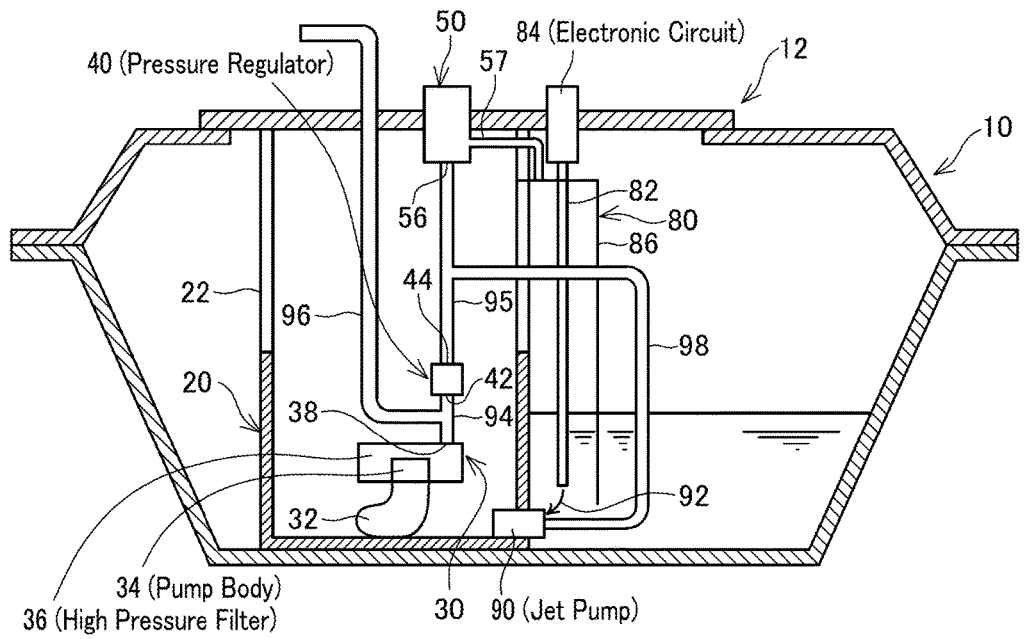
FIG. 7 shows a configuration around a fuel tank according to a seventh embodiment.

The seventh embodiment shown in FIG. 7 is a combination of the fourth embodiment of FIG. 4 and the sixth embodiment of FIG. 6.

(Eighth Embodiment of Structure Around Fuel Tank 10)

Figure 8:
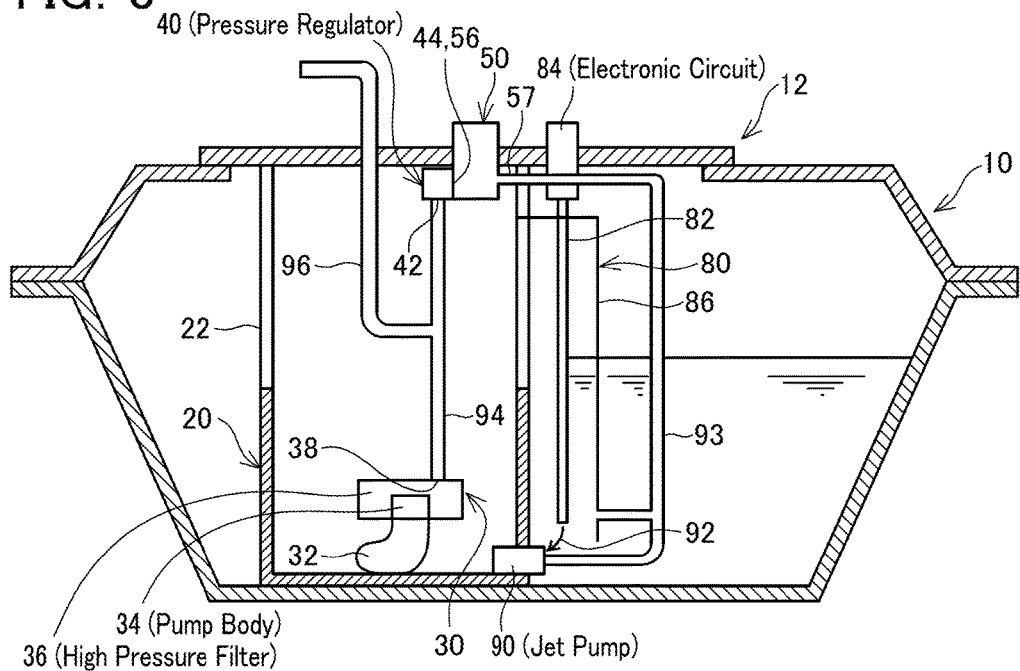
FIG. 8 shows a configuration around a fuel tank according to an eighth embodiment.

The eighth embodiment shown in FIG. 8 is a combination of the third embodiment of FIG. 3 and the sixth embodiment of FIG. 6. In the eighth embodiment, the fuel having passed through the capacitance measuring device 50 is returned to the case 86 at a position under the case 86. According to this embodiment, it is possible to prevent an error in the measured liquid level due to the fact that the fuel having passed through the capacitance measuring device 50 flows down along the surface of the liquid level measuring sensor substrate 82.

Moreover, as indicated by arrow 92, the jet pump 90 returns the fuel in the case 86 into the reserve cup 20. In this manner, the flow of the fuel circulating through the fuel pump 30, the capacitance measuring device 50, and the liquid level measuring device 80 is accelerated. Thus, it is possible to obtain such a relation that the quality of the fuel measured by the capacitance measuring device 50 is identical to the quality of the fuel measured by the liquid level measuring device 80.

(Second Embodiment of Capacitance Measuring Device 50)

Figure 10:
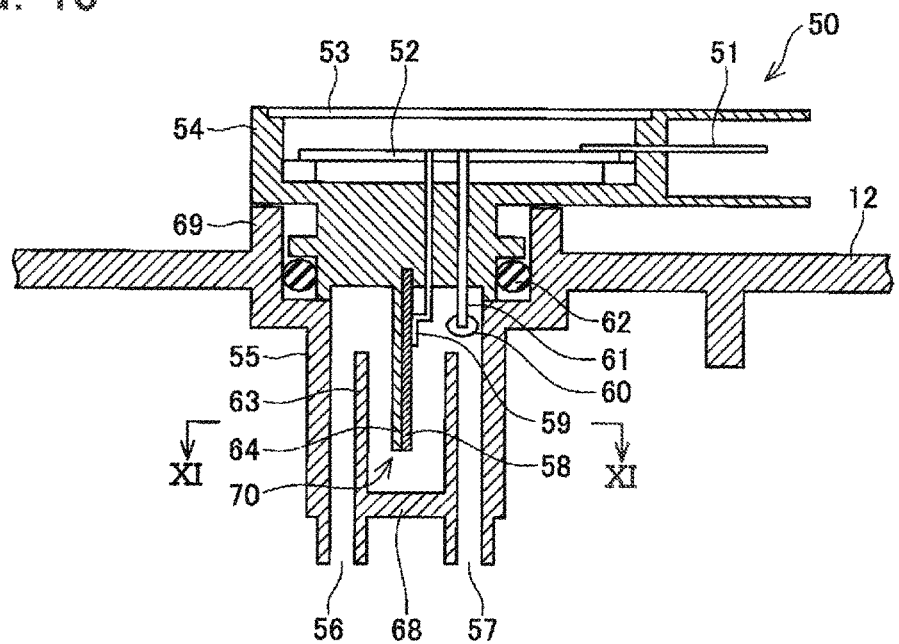
FIG. 10 shows a configuration of a capacitance measuring device according to the second embodiment.
Figure 11:
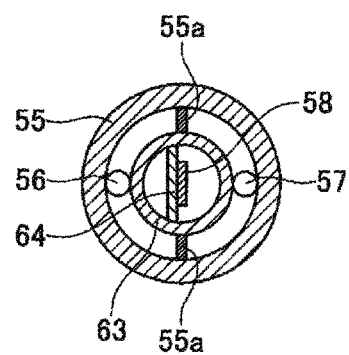
FIG. 11 shows a XI-XI cross section of FIG. 10.

As shown in FIG. 10, in this embodiment, a cylindrical wall 63 is formed on the bottom plate 68 so as to extend upward. Moreover, as shown in FIG. 11, a separation wall 55a is formed between the outer cylindrical wall 55 and the inner cylindrical wall 63. The separation wall 55a separates the inlet port 56 and the outlet port 57.

Moreover, the sensor substrate 58 is fixed to a partition wall 64, and the partition wall 64 partitions the inner cylindrical wall 63 into two spaces along the diameter of the inner cylindrical wall 63. However, the lower end of the partition wall 64 is open.

In this embodiment, the fuel discharged from the pressure regulator 40 reaches the surface of the sensor substrate 58 while passing through the inlet port 56, the left half between the outer cylindrical wall 55 acrd the heeler cylindrical wall 63, the left half of the inner space of the inner cylindrical wall 63, and the lower end of the partition wall 64. According to this configuration, the fuel can smoothly pass through the fuel-measuring storage chamber 70, and bubbles included in the fuel can be prevented from adhering to the surface of the sensor substrate 58. Thus, no error is introduced in the course of calculating the permittivity of the fuel from the capacitance.

(Modification of Capacitance Measuring Device 50)

Figure 12:
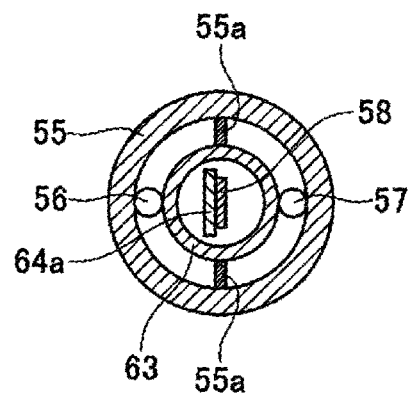
FIG. 12 shows a modification of FIG. 11.

As shown in FIG. 12, the partition wall 64 may not necessarily partition the inner cylindrical wall 63 completely, but such a partition wall 64a that a gap remains between both ends and the inner cylindrical wall 63 may be used.

(Modification of Capacitance Measuring Device 50)

Figure 13:
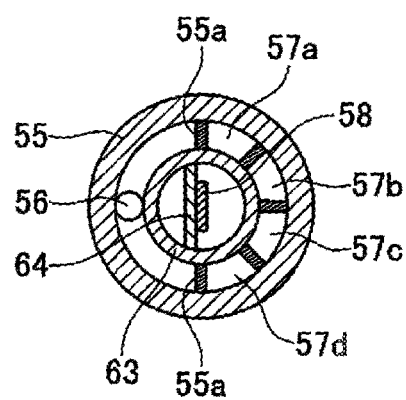
FIG. 13 shows another modification of FIG. 11.

As shown in FIG. 13, a plurality of outlet ports 57a, 57b, 57c, and 57d may be formed.

(Third Embodiment of Capacitance Measuring Device 50)

Figure 14:
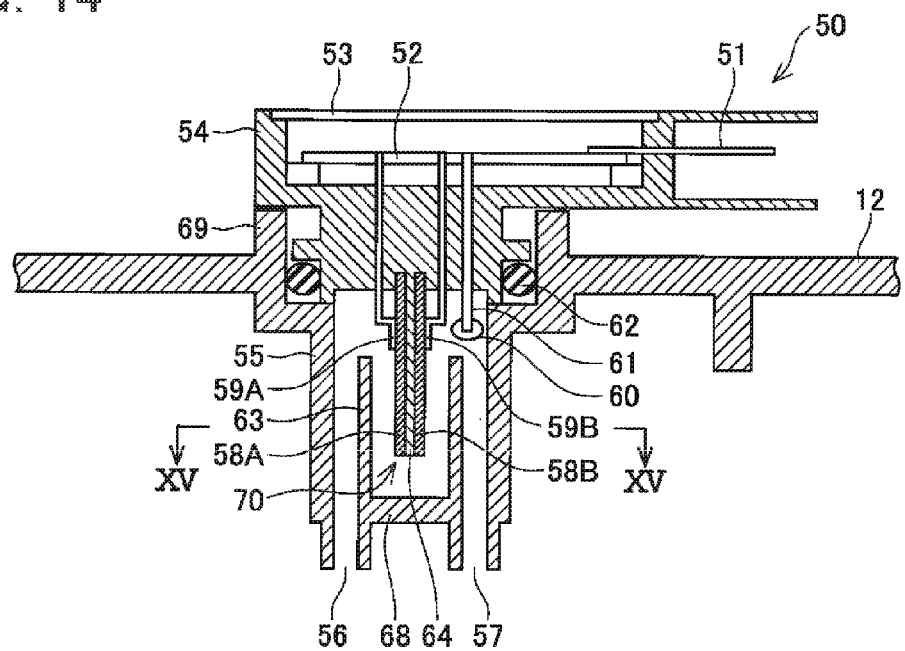
FIG. 14 shows a configuration of a capacitance measuring device according to the third embodiment.
Figure 15:
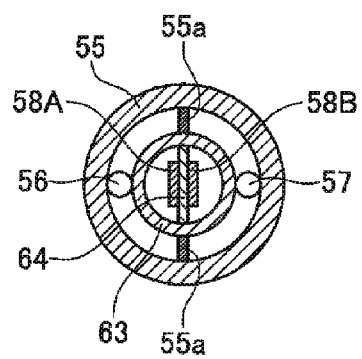
FIG. 15 shows a XV-XV cross section of FIG. 14.

As shown in FIGS. 14 and 15, sensor substrates 58A and 58B may be disposed on both surfaces of the partition wall 64. As a result, the capacitance to be measured is doubled, and measurement accuracy is improved.

(Fourth Embodiment of Capacitance Measuring Device 50)

Figure 16:
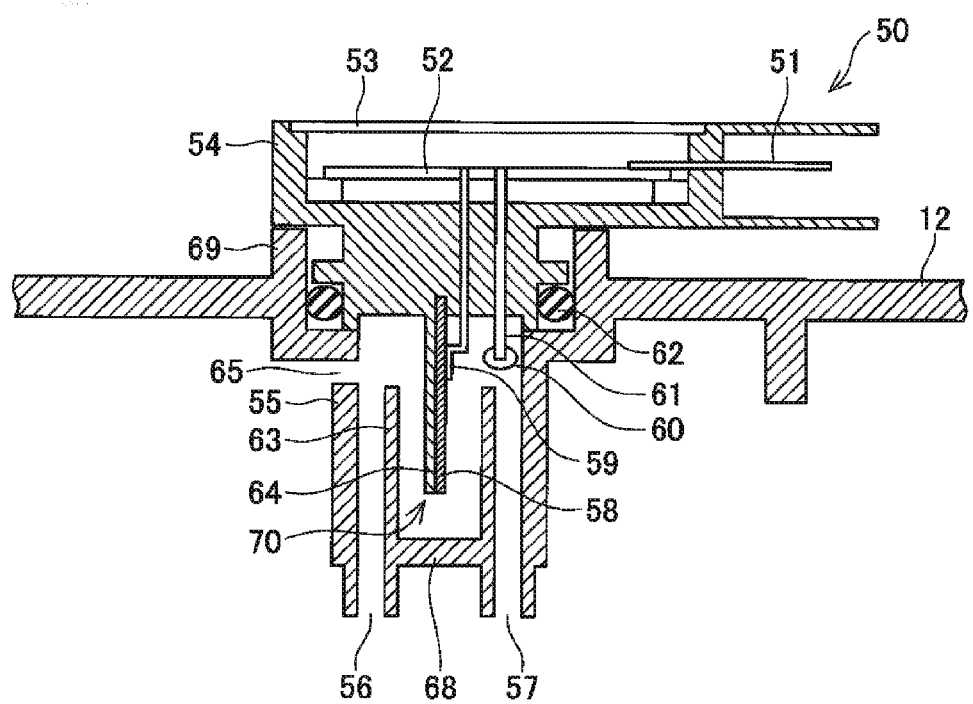
FIG. 16 shows a configuration of a capacitance measuring device according to the fourth embodiment.

In this embodiment, as shown in FIG. 16, an opening 65 is formed above the inlet port 56 of the cylindrical wall 55. Bubbles may be mixed into the fuel discharged from the pressure regulator 40. When the opening 65 is formed above the inlet port 56, the opening 65 becomes a degassing port, and the bubbles included in the fuel will not reach the surface of the sensor substrate 58.

(Fifth Embodiment of Capacitance Measuring Device 50)

Figure 17:
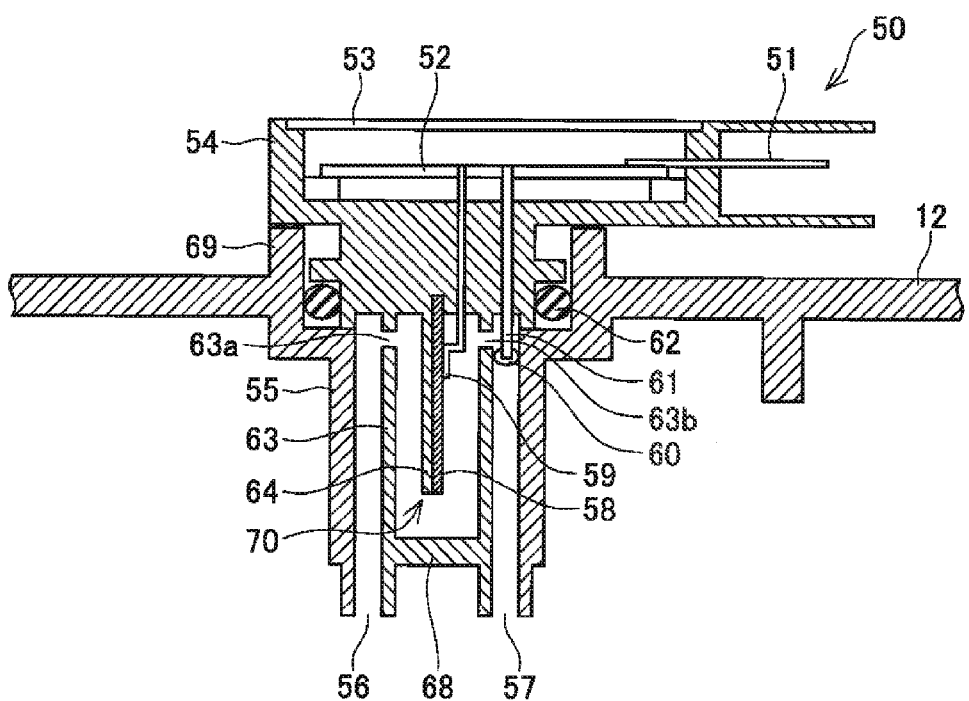
FIG. 17 shows a configuration of a capacitance measuring device according to the fifth embodiment.

As shown in FIG. 17, the inner cylinder 63 may be formed integrally with the sensor body 54. In this case, when openings 63a and 63b are formed above the inner cylinder 63, it is possible to obtain such a relation that the fuel discharged from the pressure regulator 40 passes through the fuel-measuring storage chamber 70.

(Sixth Embodiment of Capacitance Measuring Device 50)

Figure 18:
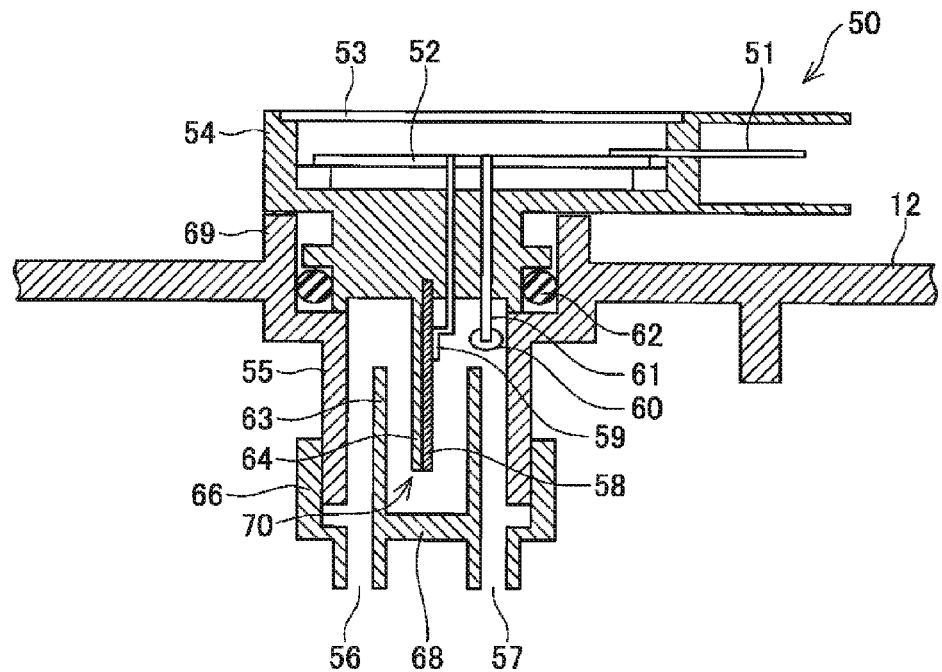
FIG. 18 shows a configuration of a capacitance measuring device according to the sixth embodiment.

As shown in FIG. 18, a bottom member 66 may be provided separately from the set plate 12. When the inlet port 56 and the outlet port 57 are formed in the bottom member 66, the shape of the set plate 12 is prevented from becoming excessively complicated.

(Seventh Embodiment of Capacitance Measuring Device 50)

Figure 19:
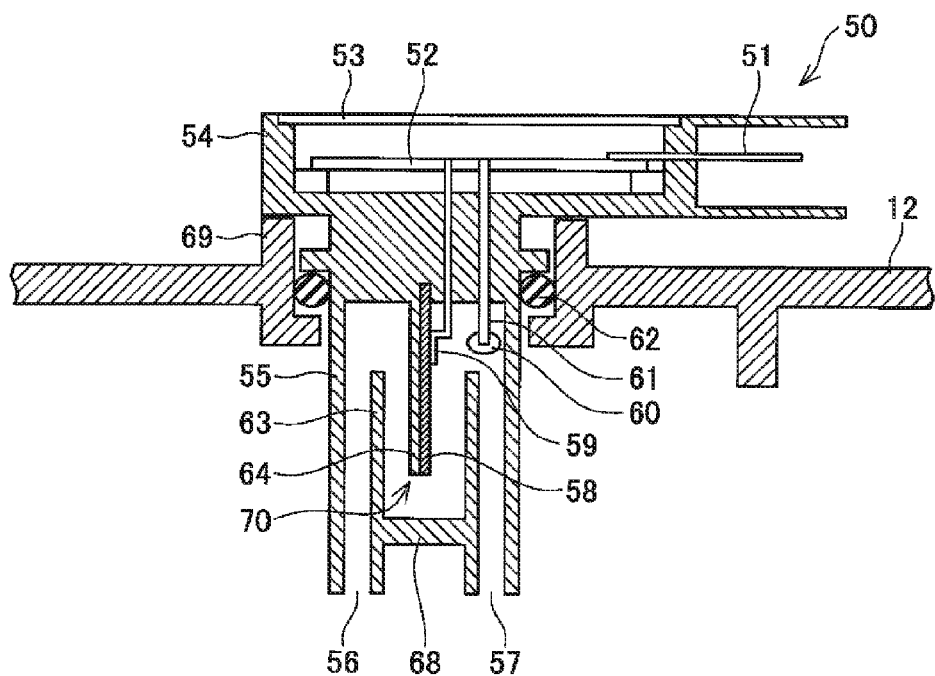
FIG. 19 shows a configuration of a capacitance measuring device according to the seventh embodiment.

As shown in FIG. 19, both the outer cylinder 55 and the inner cylinder 63 may be formed integrally with the sensor body 54.

(Eighth Embodiment of Capacitance Measuring Device 50)

Figure 20:
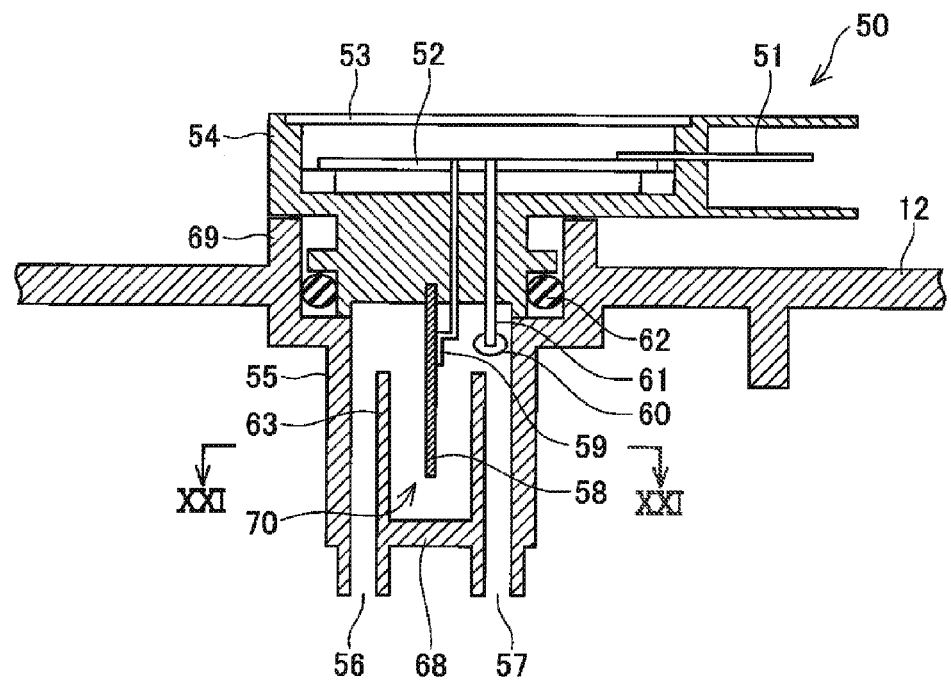
FIG. 20 shows a configuration of a capacitance measuring device according to the eighth embodiment.
Figure 21:
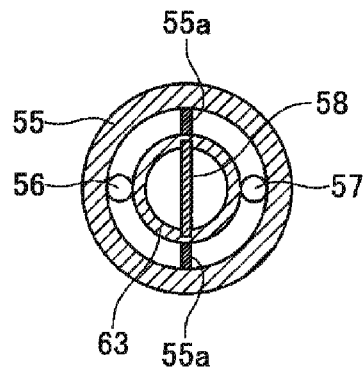
FIG. 21 shows a XXI-XXI cross section of FIG. 20.

As shown in FIGS. 20 and 21 the sensor substrate 58 itself inserted in the inner cylinder 63 may be used as a partition wail. The left and right end portions of the sensor substrate 58 may support the inner cylinder 63.

(Ninth Embodiment of Capacitance Measuring Device 50)

Figure 22:
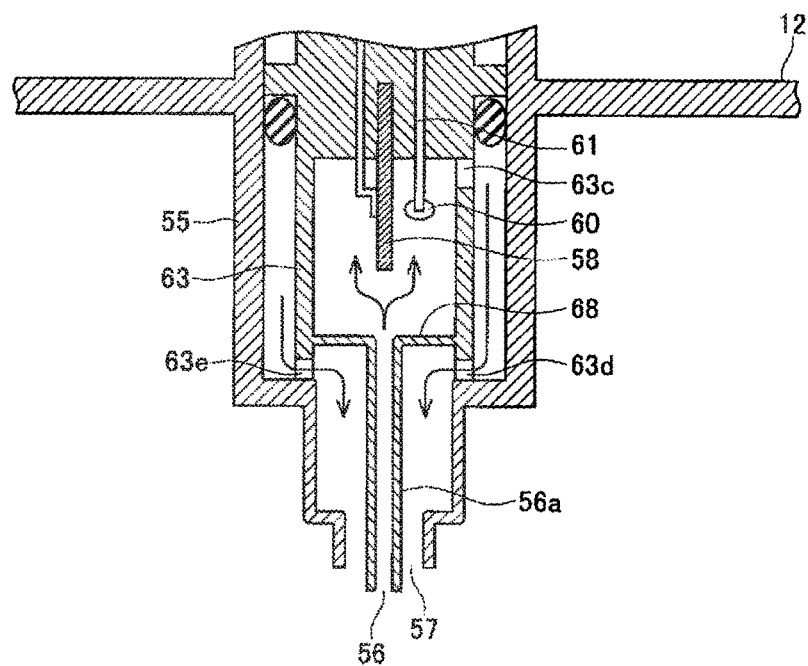
FIG. 22 shows a configuration of a capacitance measuring device according to a ninth embodiment.

As shown in FIG. 22, the inlet port 56 and the outlet port 57 may be concentric. In this case, a pipe 56a is formed so as to extend from the center of the bottom 68 of the inner cylinder 63 to the inlet port 56. Moreover, an opening 63c is formed above the inner cylinder 63 so that fuel leaks outside the inner cylinder 63. Further, the bottom 68 is lifted, and openings 63d and 63e are formed in the cylinder 63 located under the bottom 68. Furthermore, the outlet port 57 is formed at the center of the bottom of the outer cylinder. The outlet port 57 has a larger diameter than the inlet port 56.

In this embodiment, the fuel discharged from the outlet port 57 flows down along the outside of the pipe that guides the fuel to the inlet port 56 and silently returns into the fuel tank 10. Thus, silence properties are improved.

(Tenth Embodiment of Capacitance Measuring Device 50)

In the following embodiments, the pressure regulator 40 and the capacitance measuring device 50 are integrated and are fixed to the set plate 12. These embodiments correspond to the embodiments of FIGS. 2 and 8.

Figure 23:
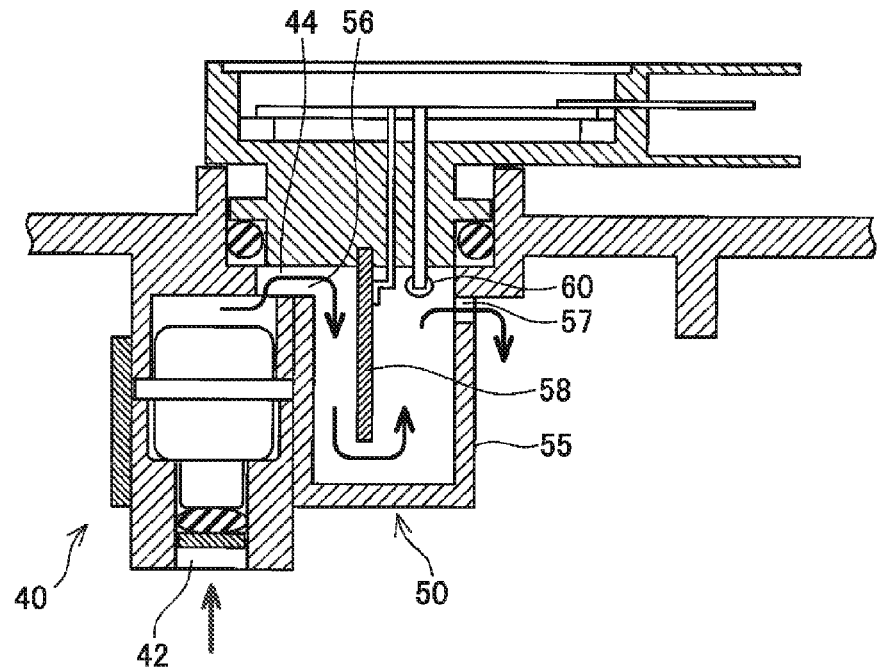
FIG. 23 shows a configuration of a capacitance measuring device according to a tenth embodiment.

In the tenth embodiment of FIG. 23, the inlet port 42 of the pressure regulator 40 faces downward. The outlet port 44 of the pressure regulator 40 communicates directly with the inlet port 56 of the capacitance measuring device 50. The outlet port 57 of the capacitance measuring device 50 is formed above the cylindrical wall 55.

(Eleventh Embodiment of Capacitance Measuring Device 50)

Figure 24:
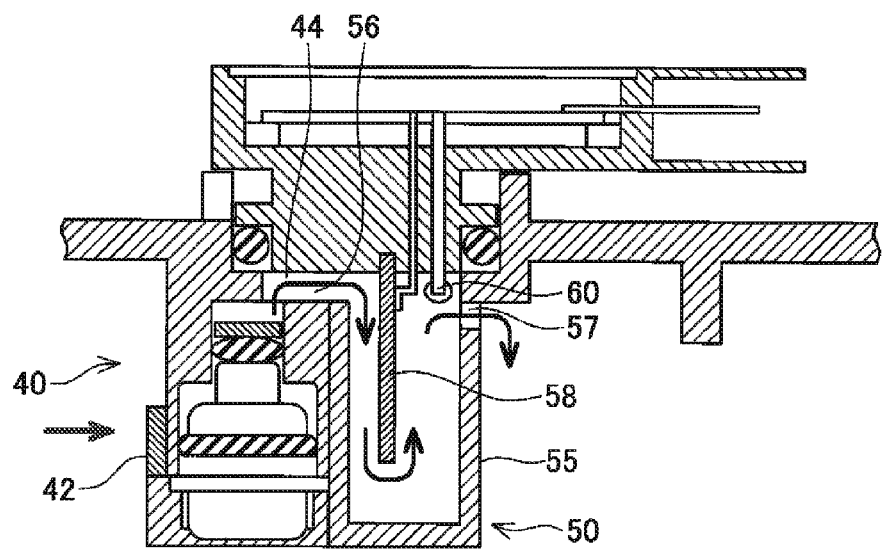
FIG. 24 shows a configuration of a capacitance measuring device according to an eleventh embodiment.

In the eleventh embodiment of FIG. 24, the inlet port 42 of the pressure regulator 40 faces laterally. The other configuration is the same as that of the embodiment of FIG. 23.

(Twelfth Embodiment of Capacitance Measuring Device 50)

Figure 25:
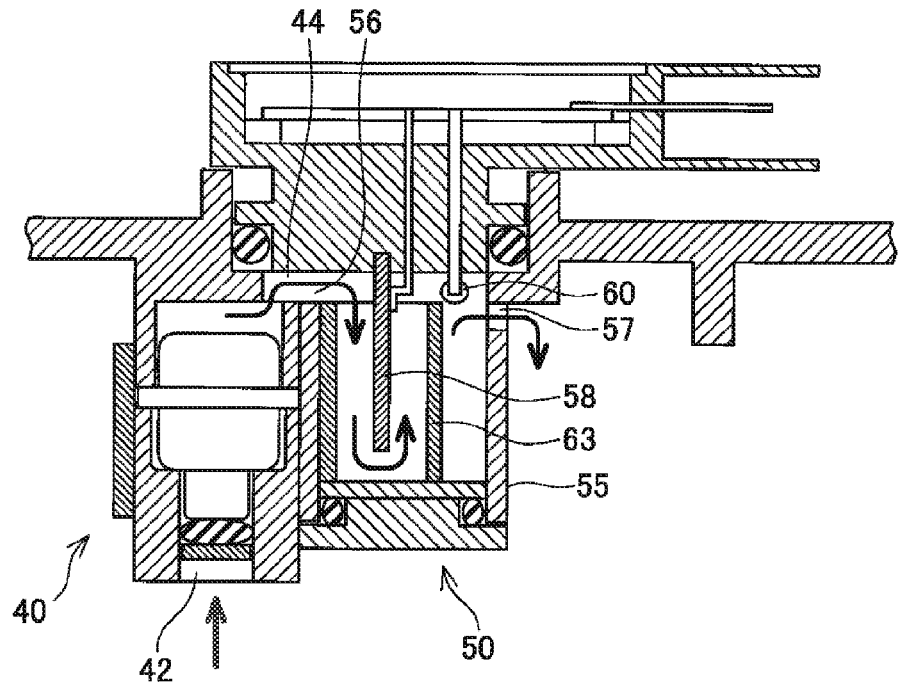
FIG. 25 shows a configuration of a capacitance measuring device according to a twelfth embodiment.

In the twelfth embodiment of FIG. 25, the sensor substrate 58 is accommodated in the cylindrical wall 63, and the cylindrical wall 63 is made from metal. Since the sensor substrate 58 is surrounded by the metal wall 63 that serves as an electromagnetic shield, the capacitance measurement result is not affected by the ambient electromagnetic noise.

(Thirteenth Embodiment of Capacitance Measuring Device 50)

Figure 26:
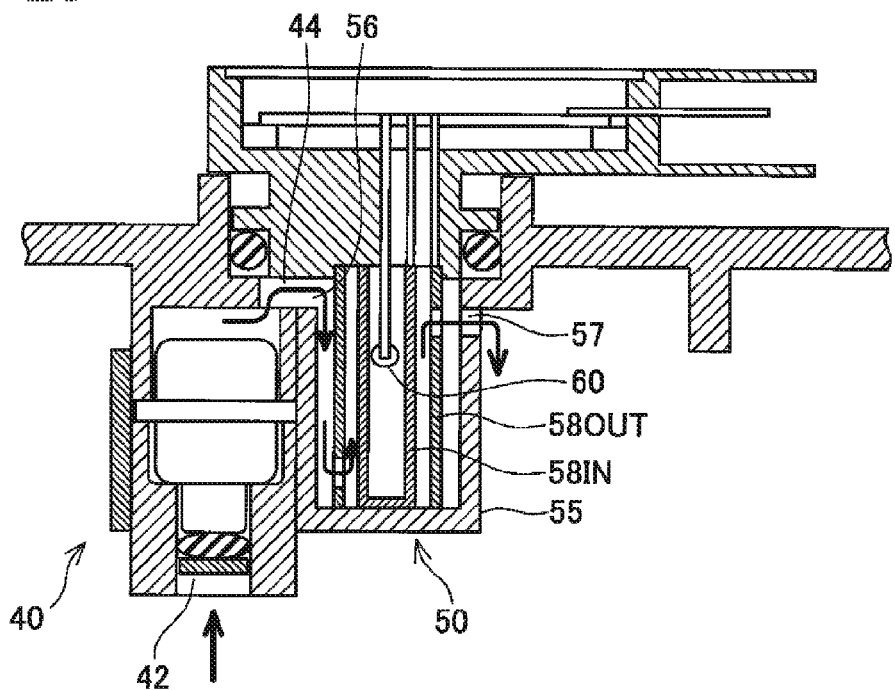
FIG. 26 shows a configuration of a capacitance measuring device according to a thirteenth embodiment.

In the thirteenth embodiment of FIG. 26, a pair of electrodes used for measuring the capacitance comprises an inner electrode 58IN and an outer electrode 58OUT. The inner electrode 58IN and the outer electrode 58OUT are made from a columnar metal material, and the outer electrode 58OUT has a larger diameter than the inner electrode 58IN. The inner electrode 58IN is disposed on the inner side and concentrically with the outer electrode 58OUT. A cylindrical space is secured between the inner electrode 58IN and the outer electrode 58OUT, and the space is filled with fuel. It is possible to measure the permittivity of the fuel filling the space between the inner electrode 58IN and the outer electrode 58OUT from the capacitance between the inner electrode 58IN and the outer electrode 58OUT.

The shape of the pair of electrodes used for the permittivity of fuel is not particularly limited.

(Fourteenth Embodiment of Structure Around Fuel Tank 10)

Figure 27:
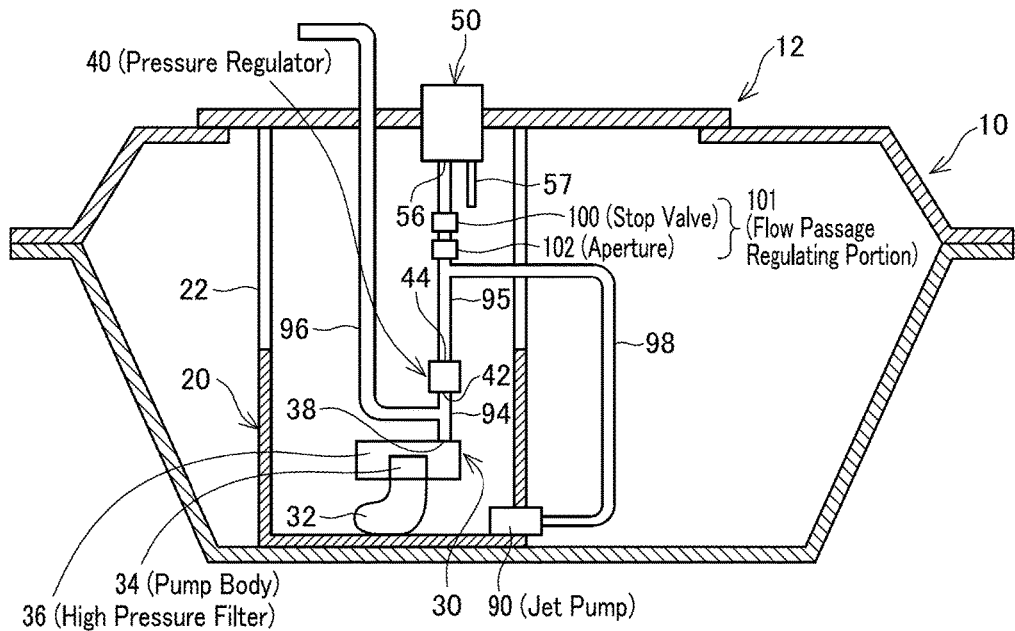
FIG. 27 shows a configuration around a fuel tank according to a fourteenth embodiment.

The fourteenth embodiment of FIG. 27 is different from the fourth embodiment of FIG. 4, in that the pipe 95 comprises a flow passage regulating portion 101 that comprises an aperture 102 and a stop valve 100. The other configuration is the same as that of the fourth embodiment, redundant description thereof will not be provided.

The aperture 102 decreases the flow passage area of the pipe 95. Due to this, the flow passage area of the pipe 95 at a position where the aperture 102 is disposed can be made smaller than the flow passage area of the pipe 98. The stop valve 100 switches between a closed state where it closes the pipe 95 and an open state where it opens the pipe 95. Specifically, when the pressure applied from the fuel in the pipe 95 to the stop valve 100 (that is, the pressure of the fuel in the pipe 95) is smaller than a predetermined value (for example, 200 Pa), the stop valve 100 is maintained in the closed state. Moreover, when the pressure of the fuel in the pipe 95 increases from the value smaller than the predetermined value to the predetermined value or more, the stop valve 100 switches from the closed state to the open state, and the stop valve 100 is maintained in the open state for a period where the pressure of the fuel in the pipe 95 is maintained at the predetermined value or more. According to this configuration, it is possible to suppress a decrease in the pressure of the fuel delivered to the jet pump 90. In a modification, the flow passage regulating portion 101 may comprise only one of the aperture 102 and the stop valve 100. Moreover, the number of apertures 102 and stop valves 100 disposed in the flow passage regulating portion 101 is not particularly limited. Further, the flow passage regulating portion 101 may be a valve of a type other than the stop valve 100, such as a valve which is electrically controlled to be open or closed.

Moreover, at least a portion of the inner diameter of the pipe 95 located closer to the capacitance measuring device 50 than the branching point of the pipe 98 may be smaller than the inner diameter of the other portions of the pipe 95 and the inner diameter of the pipe 98. With this configuration, it is possible to obtain the same advantages as those when the aperture 102 is disposed.

(Fifteenth Embodiment of Structure Around Fuel Tank 10)

Figure 28:
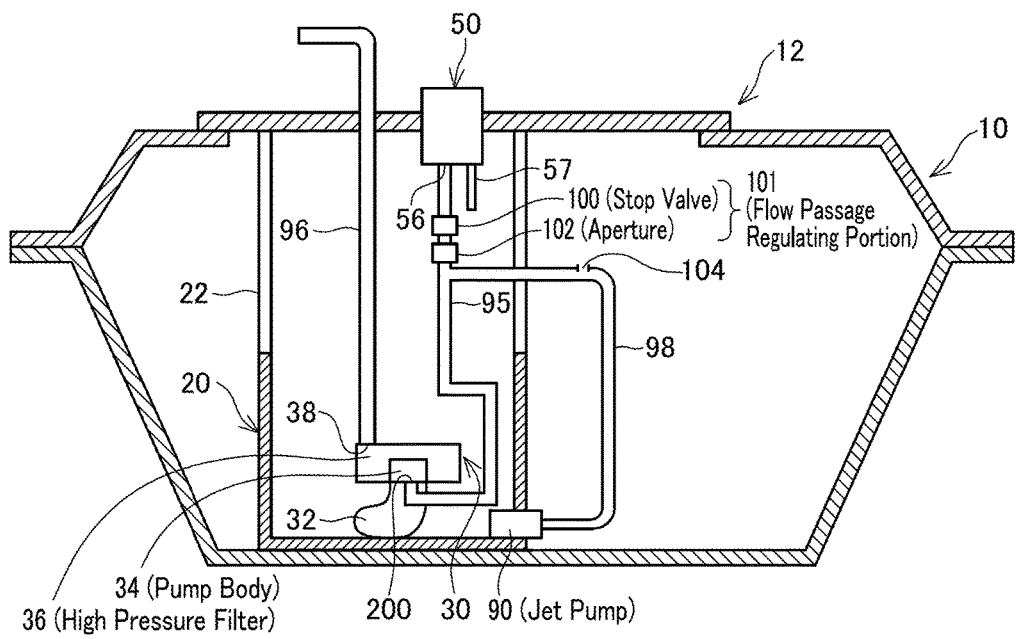
FIG. 28 shows a configuration around a fuel tank according to a fifteenth embodiment.

The fifteenth embodiment of FIG. 28 is different from the fourteenth embodiment of FIG. 27 in that the pipe 95 is connected to a vapor jet 200 of the fuel pump 30. The other configuration is the same as that of the fourteenth embodiment, and redundant description thereof will not be provided. In the fifteenth embodiment, a pressure regulator (not shown) is provided at an intermediate position of the pipe 96.

The vapor jet 200 allows the fuel flow passage within the fuel pump 30 to communicate with the outside of the fuel pump 30. The vapor jet 200 is a communication passage for discharging bubbles of the fuel in the fuel pump 30 to the outside of the fuel pump 30. Fuel pressurized by the fuel pump 30 is discharged from the vapor jet 200. The fuel discharged from the vapor jet 200 flows into the pipe 95.

A communication hole 104 is formed at an intermediate position of the pipe 98. The communication hole 104 allows the inside of the pipe 98 to communicate with the inside of the fuel tank 10. When the fuel pump 30 stops after driving, the fuel pipes 95 and 98 are filled with fuel. Due to the communication hole 104, it is possible to suppress a so-called siphon phenomenon in which the fuel in the pipes 95 and 98 flows from the jet pump 90 toward the fuel pump 30.

(Modifications of Fourteenth and Fifteenth Embodiments)

Figure 29:
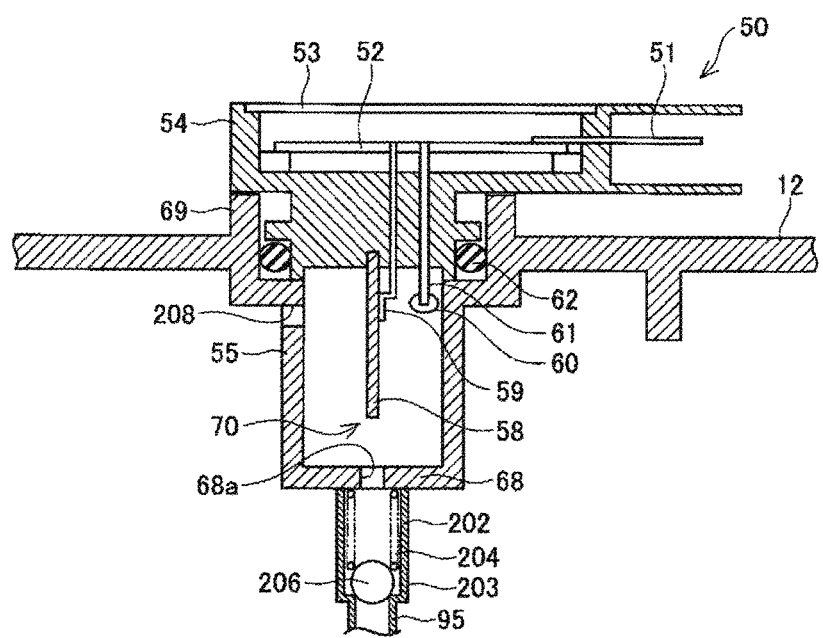
FIG. 29 shows a configuration of a capacitance measuring device according to a modification.
Figure 30:
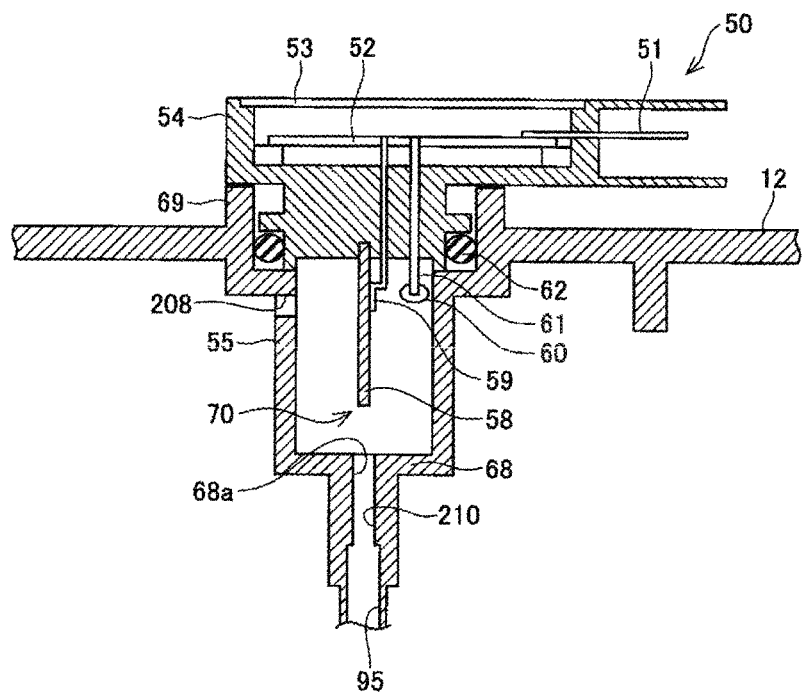
FIG. 30 shows a configuration of a capacitance measuring device according to a modification.
Figure 31:
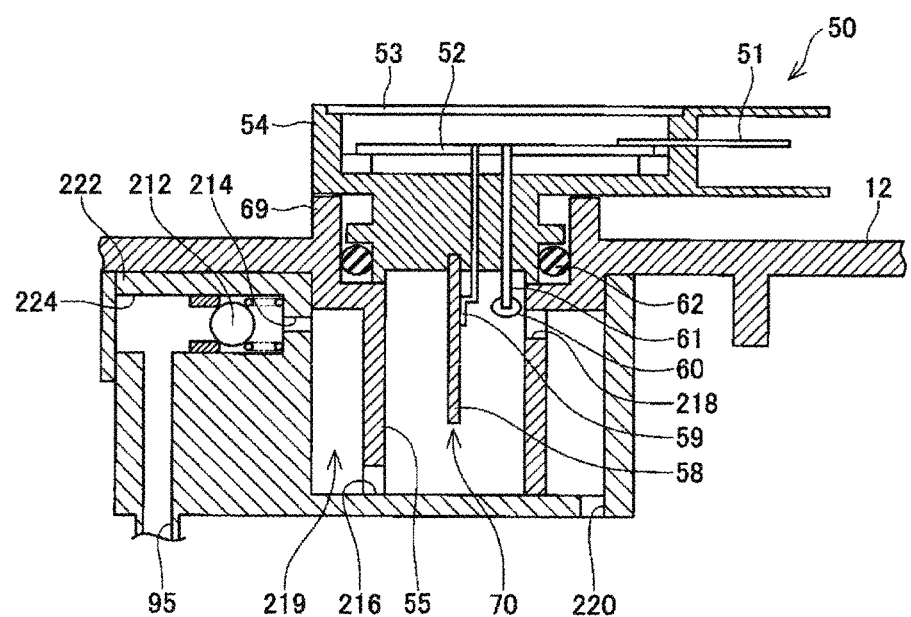
FIG. 31 shows a configuration of a capacitance measuring device according to a modification.

(1) In the fourteenth and fifteenth embodiments, the flow passage regulating portion 101 is disposed in the pipe 95. However, as shown in FIGS. 29 to 31, for example, the flow passage regulating portion may be configured to be integrated with the set plate 12. In FIG. 29, a stop valve 202 which is a flow passage regulating portion is configured to be integrated with the bottom 68 that defines the fuel-measuring storage chamber 70. The stop valve 202 comprises a spherical valve body 206, a coil spring 204, and a barrel 203. The barrel 203 communicates with the pipe 95 and the inlet port 68a of the bottom 68. The barrel 203 accommodates the valve body 206 and the coil spring 204. The valve body 206 is biased toward an end portion of the pipe 95 by the coil spring 204. When predetermined pressure is applied from the pipe 95 to the valve body 206, the valve body 206 is separated from the end portion of the pipe 95, and the stop valve 202 is opened. As a result, the pipe 95 and the fuel-measuring storage chamber 70 communicate with each other, and fuel flows into the fuel-measuring storage chamber 70. In this modification, an outlet port 208 may be formed in the cylindrical wall 55 instead of the outlet port 57. According to this configuration, it is possible to easily dispose the flow passage regulating portion within the fuel tank 10. In this case, the aperture 102 may be provided in the pipe 95.

(2) In FIG. 30, an aperture 210 which is a flow passage regulating portion is configured to be integrated with the bottom 68 that defines the fuel-measuring storage chamber 70. The aperture 210 communicates with the pipe 95 and the inlet port 68a of the bottom 68. A flow passage area of the aperture 201 is smaller than the flow passage area of the pipe 95. According to this configuration, it is possible to easily dispose the flow passage regulating portion within the fuel tank 10, in this case, the stop valve 100 may be provided in the pipe 95.

(3) In FIG. 31, a stop valve 212 which is a flow passage regulating portion is disposed in an accommodation wall 222 that accommodates the cylindrical wall 55. The accommodation wall 222 is configured to be integrated with the set plate 12. The accommodation wall 222 and the set plate 12 form a space 219 that accommodates the cylindrical wall 55. The accommodation wall 222 closes the lower end of the cylindrical wall 55. The accommodation wall 222 comprises a fuel passage 224 that is connected to the pipe 95. The fuel passage 224 communicates with the space 219 via an opening 214. A flow passage area of the opening 214 is smaller than the flow passage area of the fuel passage 224. That is, the opening 214 has the function of an aperture. Due to this, the opening 214 decreases the pressure of the fuel in the fuel passage 224 and the opening 214. According to this configuration, it is possible to easily provide the fuel passage 224 and the opening 214 in the fuel tank. Moreover, the stop valve 212 is disposed in the fuel passage 224. The stop valve 212 has the same configuration as the stop valve 202. When predetermined pressure is applied from the fuel passage 224 to the valve body of the stop valve 212, the stop valve 212 is opened. As a result, the fuel passage 224 and the space 219 communicate with each other, and fuel flows into the space 219. The fuel flowing into the space 219 passes through an opening 216 formed in the cylindrical wall 55, flows into the fuel-measuring storage chamber 70, passes through an opening 218 formed in the cylindrical wall 55 and an opening 220 formed in the accommodation wall 222, and is finally discharged outside the space 219. In this case, the aperture 102 may be provided in the fuel pipe 95.

(Sixteenth Embodiment of Structure Around Fuel Tank 10)

Figure 32:
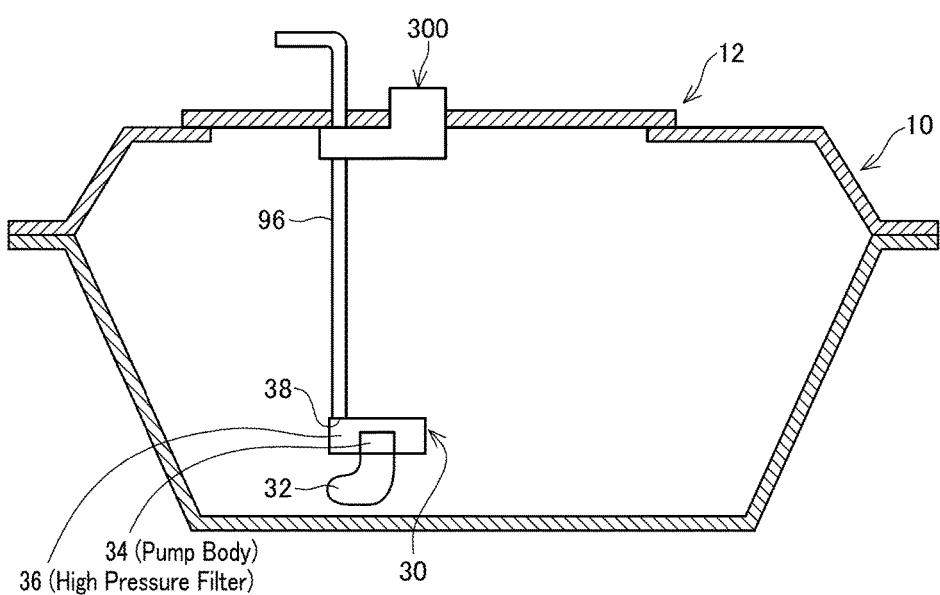
FIG. 32 shows a configuration around a fuel tank according to a sixteenth embodiment.

The sixteenth embodiment of FIG. 32 is different from the first embodiment of FIG. 1, in that the fuel-measuring storage chamber 70 communicates with the pipe 96. In the sixteenth embodiment, the fuel discharged from a pressure regulator (not shown) is discharged into the fuel tank 10 without passing through the fuel-measuring storage chamber 70.

Figure 33:
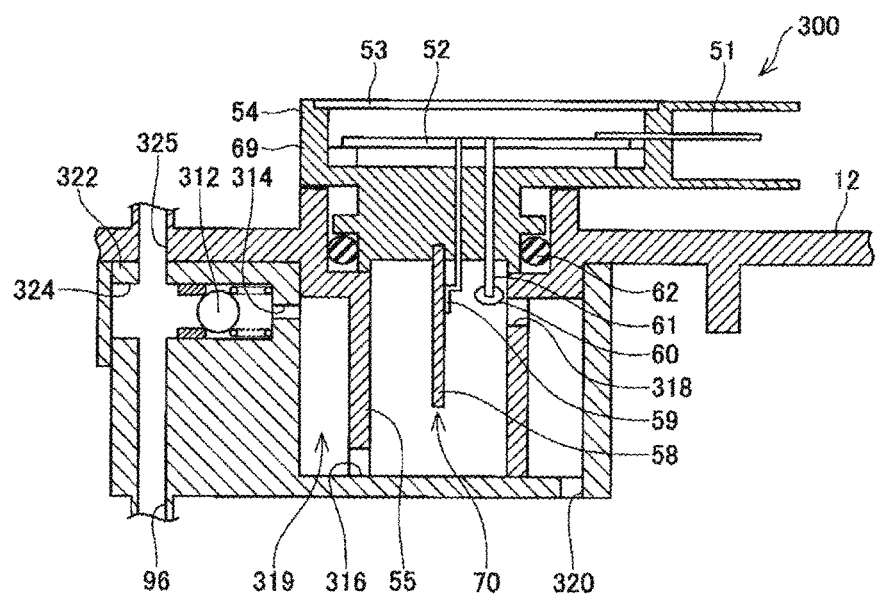
FIG. 33 shows a configuration of a capacitance measuring device according to the sixteenth embodiment.

As shown in FIG. 33, an accommodation wall 322 is integrally attached to the set plate 12. The accommodation wall 322 has the same configuration as the accommodation wall 222 of FIG. 31. That is, the accommodation wall 322 comprises a branch passage 324, a stop valve 312, and openings 314, 316, 318, and 320. Moreover, the accommodation wall 322 comprises a communication passage 325 that passes through the accommodation wall 322. The fuel in the pipe 96 passes through the communication passage 325 and is then discharged outside the fuel tank 12 and supplied to the engine. The branch passage 324 branches off from the communication passage 325. The branch passage 324 communicates with a space 319 via the opening 314 similarly to the fuel passage 224. A flow passage area of the opening 314 is made smaller by the flow passage area of the branch passage 324. Due to this, the opening 214 decreases the pressure of the fuel in the branch passage 324. In the case of the stop valve 312 of the branch passage 324, when predetermined pressure is applied from the branch passage 324 to the valve body of the stop valve 312, the stop valve 312 is opened. As a result, the branch passage 324 and the space 319 communicate with each other, and fuel flows into the space 319. Due to the stop valve 312, it is possible to suppress a decrease in the pressure of the fuel supplied to the engine through the communication passage 325. The fuel flowing into the space 319 passes through the opening 316 formed in the cylindrical wall 55, flows into the fuel-measuring storage chamber 70, passes through the opening 318 formed in the cylindrical wall 55 and the opening 320 formed in the accommodation wall 322, and is then discharged outside the space 319. In this modification, the stop valve 312 may not be disposed.

(Modification of Sixteenth Embodiments)

In the sixteenth embodiment, the fuel flow passage that branches off from the pipe 96 and reaches the fuel-measuring storage chamber 70 is formed by the accommodation wall 322 that is integrated with the set plate 12. However, the fuel flow passage that branches off from the pipe 96 and reaches the fuel-measuring storage chamber 70 may not be integrated with the set plate 12. For example, a pipe that extends from an intermediate position of the pipe 96 to the fuel-measuring storage chamber 70 may be disposed. In this case, the pipe may comprise at least one of a stop valve and an aperture.

(Modifications)

(1) The measuring devices 50 and 350 of the fourteenth and sixteenth embodiments may comprise the liquid level measuring device 80. In this case, the fuel discharged from the fuel-measuring storage chamber 70 may flow into the case 86 of the liquid level measuring device 80.

(2) The electrodes of the respective embodiments are not limited to the electrodes described in the respective embodiments. For example, the electrodes may be a pair of cylindrical electrodes and may be a pair of flat plate-like electrodes.

(3) In the fourteenth and fifteenth embodiments, the pipe 98 that delivers fuel to the jet pump 90 branches off from the pipe 95 that delivers fuel to the capacitance measuring device 50. However, the pipe 95 may not branch off.

(4) In the fourteenth and fifteenth embodiments, a three-way valve may be disposed at the branching point between the pipe 95 and the pipe 98.

What is claimed is:

1. A measuring device configured to measure a property of fuel supplied from a fuel tank to outside of the fuel tank, the measuring device comprising:
   a fuel pump configured to suck the fuel in the fuel tank and deliver the sucked fuel;
   a fuel supply pipe configured to supply the fuel delivered by the fuel pump to the outside of the fuel tank;
   a fuel-measuring storage chamber comprising an outlet port communicating an inside of the fuel tank and an inside of the fuel-measuring storage chamber, and configured to store the fuel delivered from the fuel pump and to return the fuel to an inside of the fuel tank, wherein low-pressure fuel that is open to the atmosphere is introduced into the fuel-measuring storage chamber;
   a first fuel pipe being different from the fuel supply pipe, connected between the fuel pump and the fuel-measuring storage chamber, and configured to be disposed in the fuel tank; and
   a pair of electrodes disposed within the fuel-measuring storage chamber so as to measure capacitance.

2. The measuring device according to claim 1, further comprising:
   a pressure regulator configured to regulate pressure of the fuel delivered by the fuel pump to a predetermined value by discharging surplus fuel to the first fuel pipe or the fuel-measuring storage chamber.

3. The measuring device according to claim 1, wherein the first fuel pipe branches off from the fuel supply pipe, and comprises a decompressing portion that decreases the pressure of the fuel in the first fuel pipe.

4. The measuring device according to claim 1, wherein the first fuel pipe extends from a vapor jet disposed in the fuel pump, and
   the vapor jet is used for discharging vapor in the fuel pump, from the fuel pump.

5. The measuring device according to claim 1, wherein the fuel-measuring storage chamber has a shape for implementing a fuel storage function with which the fuel does not leak from the fuel-measuring storage chamber when the fuel pump stops.

6. The measuring device according to claim 5, wherein the fuel-measuring storage chamber comprises a bottomed cylinder that accommodates the pair of electrodes.

7. The measuring device according to claim 1, wherein the pair of electrodes is surrounded by an electromagnetic shield.

8. The measuring device according to claim 1, wherein the fuel-measuring storage chamber and the pair of electrodes are fixed to a set plate that closes an opening formed in the fuel tank.

9. The measuring device according to claim 1, further comprising:
a reserve cup that accommodates the fuel pump in the fuel tank;
a jet pump configured to deliver fuel outside the reserve cup into the reserve cup by utilizing a flow of the fuel delivered from the fuel pump; and
a second fuel pipe extends from the fuel-measuring storage chamber and reaches the jet pump.

10. The measuring device according to claim 1, further comprising:
a reserve cup that accommodates the fuel pump in the fuel tank;
a jet pump configured to deliver fuel outside the reserve cup into the reserve cup by utilizing a flow of the fuel delivered from the fuel pump; and
a third fuel pipe that branches from the first fuel pipe to the jet pump.

11. The measuring device according to claim 10, further comprising:
a three-way valve disposed at a branching point between the first fuel pipe and the third fuel pipe.

12. The measuring device according to claim 10, wherein a flow passage area of at least a portion of the first fuel pipe is smaller than a flow passage area of the third fuel pipe.

13. The measuring device according to claim 10, further comprising:
a flow passage regulating portion that is disposed in the first fuel pipe and comprises a valve, an aperture, or a combination thereof.

14. The measuring device according to claim 13, wherein the flow passage regulating portion is configured to be integrated with a set plate that closes an opening formed in the fuel tank.

15. The measuring device according to claim 10, further comprising:
a communication hole disposed at an intermediate position of the third fuel pipe so as to allow the third fuel pipe to communicate with the fuel tank.

16. The measuring device according to claim 3, wherein the first fuel pipe and the decompressing portion are configured to be integrated with a set plate that closes an opening formed in the fuel tank.

17. The measuring device according to claim 16, further comprising:
a valve mechanism that is disposed in the first fuel pipe so as to close the first fuel pipe in a case where pressure applied from the fuel to the valve mechanism is smaller than a predetermined value, and to open the fuel discharge passage in a case where the pressure applied from the fuel to the valve mechanism is the predetermined value or more.

18. The measuring device according to claim 1, further comprising:
a liquid level measuring device;
a case that accommodates the liquid level measuring device and has fuel permeating properties so that liquid levels inside and outside the case are equalized; and
a fourth fuel pipe that extends from the fuel-measuring storage chamber and reaches the case.

19. The measuring device according to claim 18, further comprising:
a reserve cup that accommodates the fuel pump in the fuel tank;
a jet pump configured to deliver fuel outside the reserve cup into the reserve cup by utilizing a flow of the fuel delivered from the fuel pump; and
a fifth fuel pipe that extends from the fuel-measuring storage chamber and reaches the jet pump, wherein
a suction port of the jet pump communicates with the inside of the case.

20. The measuring device as in claim 1, wherein
he fuel supply pipe is configured to extend toward an outside of the fuel tank in the fuel tank, and
the first fuel pipe is configured to extend toward the fuel-measuring storage chamber in the fuel tank.

* * * * *